US010345218B2

(12) United States Patent
Berezhna et al.

(10) Patent No.: US 10,345,218 B2
(45) Date of Patent: Jul. 9, 2019

(54) AUTOMATED SLIDE ASSESSMENTS AND TRACKING IN DIGITAL MICROSCOPY

(71) Applicant: Abbott Laboratories, Abbott Park, IL (US)

(72) Inventors: Svitlana Y. Berezhna, Los Gatos, CA (US); Rene Nieves Alicea, San Francisco, CA (US); Kam Lin Wong, Abbott Park, IL (US); Damian John Verdnik, McKinnon (AU); Leigh Whiting, Abbott Park, IL (US); Mahmoud Janbakhsh, San Ramon, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 15/832,329

(22) Filed: Dec. 5, 2017

(65) Prior Publication Data
US 2018/0156713 A1 Jun. 7, 2018

Related U.S. Application Data

(60) Provisional application No. 62/430,794, filed on Dec. 6, 2016.

(51) Int. Cl.
*G06K 9/00* (2006.01)
*G01N 15/14* (2006.01)
(Continued)

(52) U.S. Cl.
CPC ..... *G01N 15/1463* (2013.01); *G01N 15/0227* (2013.01); *G01N 15/1434* (2013.01);
(Continued)

(58) Field of Classification Search
CPC .......... G01N 15/0227; G01N 15/1463; G01N 2015/0073; G01N 15/1434;
(Continued)

(56) References Cited

U.S. PATENT DOCUMENTS 4,000,417 A 12/1976 Adkisson et al.
4,207,554 A 6/1980 Resnick et al.
(Continued)

OTHER PUBLICATIONS

Angulo and Flandrin (2003) "Automated detection of working area of peripheral blood smears using mathematical Morphology" Analytical Cellular Pathology 25: 37-49.
(Continued)

*Primary Examiner* — Tom Y Lu
(74) *Attorney, Agent, or Firm* — Edward J. Baba; Shweta H. Chandra; Bozicevic, Field & Francis LLP

(57) ABSTRACT

The present disclosure provides methods for automated slide assessments made in conjunction with digital image-based microscopy. Automated methods of acquiring patient information and specimen information from prepared slides, and digitally linking such information into patient-tagged specimen data, are provided. Also provided are methods that include automatically identifying an optimal area for morphological assessment of a blood smear on a hematological slide, including methods for triggering the analysis of such an area, e.g., using an automated digital image-based hematology system. The present disclosure also provides devices, systems and computer readable media for use in performing processes of the herein described methods.

31 Claims, 8 Drawing Sheets

(51) Int. Cl.
*G01N 15/02* (2006.01)
*G06T 7/00* (2017.01)
*G06T 7/11* (2017.01)
*G06K 9/46* (2006.01)
*G01N 15/00* (2006.01)
*G01N 15/10* (2006.01)

(52) U.S. Cl.
CPC ....... *G01N 15/1475* (2013.01); *G06K 9/4604* (2013.01); *G06T 7/0016* (2013.01); *G06T 7/11* (2017.01); *G01N 2015/0073* (2013.01); *G01N 2015/1006* (2013.01); *G01N 2015/1452* (2013.01); *G01N 2015/1465* (2013.01); *G01N 2015/1486* (2013.01); *G01N 2015/1493* (2013.01); *G01N 2015/1497* (2013.01); *G06T 2207/10056* (2013.01); *G06T 2207/30024* (2013.01); *G06T 2207/30242* (2013.01)

(58) Field of Classification Search
CPC ....... G01N 15/1475; G01N 2015/1006; G01N 2015/1452; G01N 2015/1465; G01N 2015/1486; G01N 2015/1493; G01N 2015/1497; G06K 9/4604; G06T 7/0016; G06T 7/11; G06T 2207/10056; G06T 2207/30024; G06T 2207/30242
See application file for complete search history.

(56) References Cited

U.S. PATENT DOCUMENTS

| | | | |
|---|---|---|---|
| 4,362,386 A | 12/1982 | Matsushita et al. | |
| 4,702,595 A | 10/1987 | Mutschler et al. | |
| 5,287,272 A | 2/1994 | Rutenberg et al. | |
| 5,671,288 A | 9/1997 | Wilhelm et al. | |
| 8,538,122 B2 | 9/2013 | Schlarb et al. | |
| 8,996,570 B2 | 3/2015 | Stratman et al. | |
| 9,384,192 B2 | 7/2016 | Wrenn et al. | |
| 2004/0223632 A1* | 11/2004 | Olszak | G02B 21/244 382/128 |
| 2008/0020128 A1* | 1/2008 | van Ryper | G01N 1/312 427/2.11 |
| 2010/0073766 A1 | 3/2010 | Angros | |
| 2011/0110578 A1* | 5/2011 | Longo | G06T 7/0002 382/144 |
| 2012/0155739 A1 | 6/2012 | Schlarb et al. | |
| 2014/0348410 A1 | 11/2014 | Grunkin et al. | |
| 2015/0003716 A1 | 1/2015 | Lloyd et al. | |
| 2017/0176481 A1 | 6/2017 | Accurso et al. | |
| 2017/0178321 A1 | 6/2017 | Nieves Alicea et al. | |

OTHER PUBLICATIONS

Horobin and Walter (1987) "Understanding Romanowsky staining" Histochemistry 86: 331-336.
Marshall et al. (1975) "A standardized Romanowsky stain prepared from purified dyes." J Clin Pathol 28(11): 920-923.
Marshall et al. (1975) "An evaluation of some commercial Romanowsky stains" J Clin Pathol 28(8): 680-685.
Marshall et al. (1978) "Staining properties and stability of a standardised Romanowsky stain" J Clin Pathol 31(3): 280-282.
Theera-Umpon and Dhompongsa (2007) "Morphological Granulometric Features of Nucleus in Automatic Bone Marrow White Blood Cell Classification" IEEE Transactions in Information Technology in Biomedicine 11(3): 353-359.

* cited by examiner

AUTOMATED SLIDE ASSESSMENTS AND TRACKING IN DIGITAL MICROSCOPY

CROSS-REFERENCE

This application claims the benefit of U.S. Provisional Patent Application No. 62/430,794 filed Dec. 6, 2016, which application is incorporated herein by reference in its entirety.

BACKGROUND

Histological and hematological analysis of patient specimens on prepared slides remains a cornerstone of clinical medicine. Such processes, including specimen preparation as well as analysis, are becoming increasingly automated. Automated histology and hematology increase specimen throughput while decreasing the incidence of observer bias and the influence of human subjectivity on the preparation and analysis processes.

With the advancement of computers, data processing and graphic software, along with the progress in artificial neural networks, digital image based hematology systems have become routine instruments in clinical laboratories. An image based hematology system typically works in part as a cell locator providing pre-classification of cells for further verification of cells' categories and detected cellular abnormalities by a skilled operator.

By nature of the processes used to smear hematological specimens, such as blood, across a slide for analysis (e.g., to prepare a blood film on the microscopy slide), regardless of whether the smear is produced by an automated device or a human technician, the smear will include areas that are less than optimal or even insufficient for proper analysis. In addition, the smear (or blood film) shall also include a certain type of cellular distribution commonly known as a feather edge used for evaluation of certain types of blood cell parameters. The accuracy and efficiency of analysis of hematological blood smear specimens is greatly increased by identification of areas of the slide where the smear is of proper thickness for analysis and has a proper density of cell distribution, i.e., not overly dense or thick and not overly diffuse or thin. Accordingly, the automated analysis of blood smears can be improved through automated identification of areas of the slide suitable for analysis and determination of which area(s) display optimal cell dispersion characteristics for a particular analysis protocol.

Furthermore, the automation of histological specimen analysis allows for the high throughput of many specimens by a single histology laboratory. Such high rates of processing place particular importance on highly accurate and efficient specimen tracking. However, inconsistent labeling of specimen slides, e.g., as is common in clinical pathology labs present in busy environments such as large hospitals, introduces constraints on the methods available for specimen tracking. In some cases, slides may be hand labeled or annotated. Hand labeling is often not readable by devices used to extract specimen identifying information during automated analysis. In addition, hand labeling can obscure machine-readable labels rendering tracking of samples difficult. While re-labeling or overwriting hand written labels with machine-readable labels may circumvent some of these issues, doing so can discard important information provided in the hand label or introduce specimen tracking error where an incorrect label is applied during the re-labeling process.

Improvements in the identification of specimen analysis areas and in specimen information tracking promise to further advance automated processing of histological specimens and the overall functioning of automated histology and hematological analyzing systems.

SUMMARY

The present disclosure provides methods for automated slide assessments made in conjunction with digital image-based microscopy. Automated methods of acquiring patient information and specimen information from prepared slides, and digitally linking such information into patient-tagged specimen data, are provided. Also provided are methods that include automatically identifying an optimal area for morphological assessment of a blood smear on a hematological slide, including methods for triggering the analysis of such an area, e.g., using an automated digital image-based hematology system. The present disclosure also provides devices, systems and computer readable media for use in performing processes of the herein described methods.

Aspects of the present disclosure include a method of assessing a blood smear on a slide using an automated digital cell morphology analyzer, the method comprising: a) collecting a plurality of z-axis images along an optical z-axis at an initial xy-position of the blood smear by varying the distance between the slide and an objective lens; b) comparing the z-axis images of the plurality to identify a starting focal z-plane; c) moving the slide or the objective lens relative to an x-axis of the blood smear through a plurality of xy-locations; d) acquiring a plurality of z-axis images based on the starting focal z-plane at each of the plurality of xy-locations and selecting an optimal z-axis image for each xy-location; e) analyzing a region of interest (ROI) within each optimal z-axis image to extract a density distribution feature value for each ROI of each image; f) identifying a morphology assessment area of the blood smear based on a comparison of the density distribution feature values; and g) assessing the morphology assessment area using an automated digital cell morphology analyzer.

In some embodiments, the x-axis of step c) is the central line of the slide. In some embodiments, varying the distance between the slide and the objective lens is performed in distinct z-axis steps. In some embodiments, moving the slide or the objective lens relative to the x-axis of the blood smear is performed at distinct x-axis steps. In some embodiments, the comparison of the density distribution feature values comprises ranking the density distribution feature values. In some embodiments, the analyzing comprises extracting a second density distribution feature value for each ROI of each image. In some embodiments, the identifying further comprises applying a threshold based on the second density distribution value to exclude one or more images of the plurality. In some embodiments, the identifying is based on ranking each image of the plurality according to their associated extracted first cellular feature value and the second cellular feature value. In some embodiments, the processing comprises varying a size of the ROI used for analysis. In some embodiments, the x-axis and the y-axis of the ROI are varied equally. In some embodiments, the x-axis and the y-axis of the ROI are varied unequally. In some embodiments, the analyzing comprises splitting each optimal z-axis image into individual color channels. In some embodiments, the analyzing comprises separating foreground objects from background objects by generating a foreground mask for each optimal z-axis image. In some embodiments, the foreground mask is generated for the blue channel. In some embodiments, generating the foreground mask further comprises closing holes in the foreground mask. In some embodiments, generating the foreground mask further comprises noise filtering. In some embodiments, the analyzing comprises segmenting each optimal z-axis image to generate a mask of separated cells. In some embodiments, the density distribution feature value is a non-color feature. In some embodiments, the density distribution feature value is a color feature. In some embodiments, the density distribution feature value is selected from the group consisting of: a cell count, a coefficient of variation (CV) index for a cell count, a cell size, a coefficient of variation (CV) index for a cell size, an index defining a cell shape, a coefficient of variation (CV) for an index for a cell shape, an index defining central pallor of the cell, an index defining cell color, a count of overlapping cells, or a combination thereof. In some embodiments, the comparing of step b) comprises applying a fast Fourier transform. In some embodiments, the acquired plurality of z-axis images at each of the plurality of xy-locations are continuous images with no xy-spatial gaps between them. In some embodiments, the length along the x-axis of the acquired plurality of z-axis images at each of the plurality of xy-locations comprises greater than 50% of the total length of the blood smear. In some embodiments, the assessing comprises scanning the morphology assessment area at a magnification greater than that used in the collecting and acquiring steps a) and c). In some embodiments, the method further comprises a quality check, wherein an extracted density distribution feature value is compared to a reference value to determine if the blood smear is sufficient quality for assessment. In some embodiments, the reference value is a range or a threshold. In some embodiments, the reference value is a cell count threshold.

Aspects of the present disclosure include a non-transitory computer readable medium storing instructions that, when executed by a computing device, cause the computing device to perform the steps of: collecting a plurality of z-axis images along an optical z-axis at an initial xy-position of a blood smear; comparing the z-axis images of the plurality to identify a starting focal z-plane; obtaining a plurality of z-axis images based on the starting focal z-plane at distinct xy-positions along an x-axis of the blood smear; selecting an optimal z-axis image for each distinct xy-position; analyzing a region of interest (ROI) within each optimal z-axis image to extract a density distribution feature value for each ROI of each image; identifying a morphology assessment area of the blood smear based on a comparison of the density distribution feature values; and triggering assessment of the morphology assessment area by an automated hematological morphology analyzer.

In some embodiments, the non-transitory computer readable medium further stores instructions that, when executed by a computing device, cause the computing device to perform the step of ranking the density distribution feature values for each ROI of each image. In some embodiments, the analyzing further comprises extracting a second density distribution feature value for each ROI of each image. In some embodiments, the identifying further comprises applying a threshold based on the second density distribution value to exclude one or more images of the plurality.

Aspects of the present disclosure include a method of assaying a slide using an automated slide analyzer to obtain patient-tagged specimen data, the method comprising: a) transporting a slide comprising a specimen area and a patient information area through an automated slide analyzer; b) acquiring a digital image of the patient information area of the slide before, during or after the transporting, wherein the patient information area comprises visible patient information; c) capturing a digital image of the specimen area; d) storing the digital images in a computer memory; and e) digitally linking the digital image of the patient information area with the digital image of the specimen area thereby generating a patient-tagged specimen image; and f) assessing the patient-tagged specimen image to obtain patient-tagged specimen data.

In some embodiments, the visible patient information is not machine-readable. In some embodiments, the transporting comprises a change in orientation of the slide from vertical to horizontal, horizontal to vertical, or both. In some embodiments, the digital image of the patient information area is acquired when the slide is in a vertical orientation. In some embodiments, the digital image of the specimen area is acquired when the slide is in a horizontal orientation. In some embodiments, the method further comprises analyzing the patient-tagged specimen data to evaluate a clinical characteristic of the patient. In some embodiments, the transporting comprises a pause to capture the digital image of the specimen area. In some embodiments, the slide comprises a blood smear and the automated slide analyzer is an automated hematological analyzer. In some embodiments, the automated hematological analyzer is an automated hematological morphology analyzer and the patient-tagged specimen data comprises patient-tagged hematological morphology data.

Aspects of the present disclosure include an automated slide analyzer for obtaining patient-tagged specimen data, the automated slide analyzer comprising: a slide conveyor for transporting a slide comprising a specimen area and a patient information area through the automated slide analyzer on a path; a first digital imager positioned along the path for capturing a digital image of the patient information area, wherein the patient information area comprises visible patient information; a microscope positioned along or at the end of the path, the microscope comprising: an imaging stage; and a second digital imager positioned above or below the imaging stage for capturing a digital image of the specimen area; a computer memory connected to the first and second digital imagers for storing the digital image of the patient information area and the digital image of the specimen area; a processor connected to the computer memory and programed with instructions that, when executed by the processor, cause the processor to: digitally link the digital image of the patient information area with the digital image of the specimen area thereby generating a patient-tagged specimen image; and assess the patient-tagged specimen image to obtain patient-tagged specimen data.

In some embodiments, the visible patient information is not machine-readable. In some embodiments, the slide conveyor comprises a rotatable slide carrier and the path comprises a change in orientation of the slide from vertical to horizontal, horizontal to vertical, or both. In some embodiments, the first digital imager is positioned along the path before the microscope. In some embodiments, the first digital imager is positioned along the path after the microscope. In some embodiments, the processor is further programed with instructions that, when executed by the processor, cause the processor to perform a method of assessing a blood smear according to, e.g., those described above.

DEFINITIONS

Figure 1:
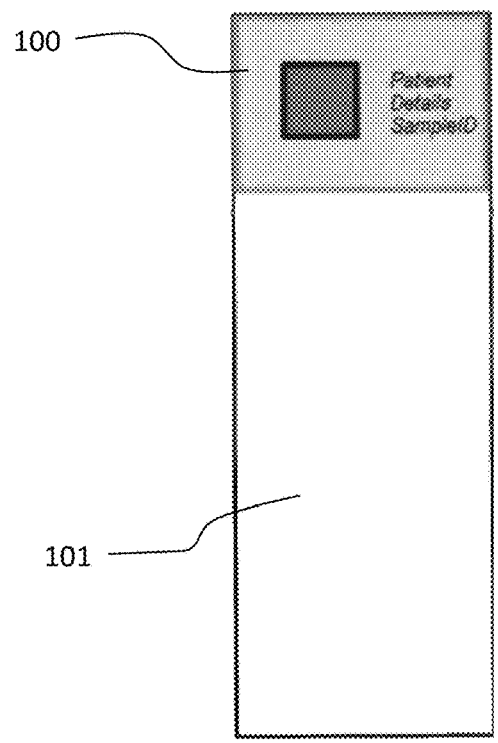
FIG. 1 depicts a microscope slide having a specimen area and a specimen information area as described herein.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the identity of" includes determining the most likely identity of a particular compound or formulation or substance, and/or determining whether a predicted compound or formulation or substance is present or absent. "Assessing the quality of" includes making a qualitative or quantitative assessment of quality e.g., through the comparisons of a determined value to a reference or standard of known quality.

The term "histology" and "histological" as used herein generally refers to microscopic analysis of the cellular anatomy and/or morphology of cells obtained from a multicellular organism including but not limited to plants and animals. As such, a "histological stain" refers to a stain used in the analysis of cellular anatomy and/or morphology and a "histology analyzer" refers to an instrument that analyzes the anatomy and/or morphology of cells obtained from a multicellular animal. As used herein a histology analyzer will generally refer to an instrument that uses one or more histological stains to make a histological assessment.

The term "bodily fluid" as used herein generally refers to fluids derived from a "biological sample" which encompasses a variety of sample types obtained from an individual or a population of individuals and can be used in a diagnostic, monitoring or screening assay. The definition encompasses blood and other liquid samples of biological origin. The definition also includes samples that have been manipulated in any way after their procurement, such as by mixing or pooling of individual samples, treatment with reagents, solubilization, or enrichment for certain components, such as nucleated cells, non-nucleated cells, pathogens, etc.

The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like.

The term "pallor" as used herein, generally refers to a lightness or pale area of a cell and most often refers to a lightness feature of red blood cells (RBCs). A "central pallor", i.e., a pale or light area at or near the center of an RBC. Central pallor may vary in size, shape and positioning as within an RBC.

The terms "control", "control assay", "control sample" and the like, refer to a sample, test, or other portion of an experimental or diagnostic procedure or experimental design for which an expected result is known with high certainty, e.g., in order to indicate whether the results obtained from associated experimental samples are reliable, indicate to what degree of confidence associated experimental results indicate a true result, and/or to allow for the calibration of experimental results. For example, in some instances, a control may be a "negative control" assay such that an essential component of the assay is excluded such that an experimenter may have high certainty that the negative control assay will not produce a positive result. In some instances, a control may be "positive control" such that all components of a particular assay are characterized and known, when combined, to produce a particular result in the assay being performed such that an experimenter may have high certainty that the positive control assay will not produce a positive result. Controls may also include "blank" samples, "standard" samples (e.g., "gold standard" samples), validated samples, etc.

The term "inputting", as used herein, is used to refer to any way of entering information into a computer, such as, e.g., through the use of a user interface. For example, in certain cases, inputting can involve selecting a feature value threshold or a reference value or library thereof that is already present on a computer system. In other cases, inputting can involve adding a threshold or a reference value to a computer system, e.g., by measuring a feature value of a sample (e.g., a sample of known quality) on a device capable of interfacing with a computer. Inputting can also be done using a user interface.

By "data processing unit", as used herein, is meant any hardware and/or software combination that will perform the functions required of it. For example, any data processing unit herein may be a programmable digital microprocessor such as available in the form of an electronic controller, mainframe, server or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based).

As used herein, the term "executing" is used to refer to an action that a user takes to initiate a program.

As used herein, the term "software" generally includes but is not limited to, one or more computer instructions and/or processor instructions that can be read, interpreted, compiled, and/or executed by a computer and/or processor. Software causes a computer, processor, or other electronic device to perform functions, actions and/or behave in a desired manner. Software may be embodied in various forms including routines, algorithms, modules, methods, threads, and/or programs. In different examples software may be embodied in separate applications and/or code from dynamically linked libraries. In different examples, software may be implemented in executable and/or loadable forms including, but not limited to, a stand-alone program, an object, a function (local and/or remote), a servelet, an applet, instructions stored in a memory, part of an operating system, and so on. In different examples, computer-readable and/or executable instructions may be located in one logic and/or distributed between multiple communicating, cooperating, and/or parallel processing logics and thus may be loaded and/or executed in serial, parallel, massively parallel and other manners.

Suitable software for implementing various components of example systems and methods described herein may be developed using programming languages and tools (e.g., Java, C, C#, C++, C, SQL, APIs, SDKs, assembler). Software, whether an entire system or a component of a system, may be embodied as an article of manufacture and maintained or provided as part of a computer-readable medium. Software may include signals that transmit program code to a recipient over a network or other communication medium. Thus, in one example, a computer-readable medium may be signals that represent software/firmware as it is downloaded from a server (e.g., web server).

A "connection" by which two components of a system, e.g., an electoral system, a data system, a computer system, circuitry system, etc., are connected will generally be an "operable connection", or a connection by which entities are "operably connected". The term "operable connection" and equivalents, is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

The term "communication" ", as used herein in relationship to "computer communication" or "data transfer", refers to a communication between computing devices (e.g., computer, server, etc.) or component of a computer system (e.g., a memory store, a digital camera, etc.) and can be, for example, a network transfer, a file transfer, an applet transfer, an email, a hypertext transfer protocol (HTTP) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, and so on.

The terms "computer" or "computer component" or "component of a computer system", as used herein, refers to a computer-related entity (e.g., hardware, firmware, software, and combinations thereof). Computer components may include, for example, a process running on a processor, a processor, an object, an executable, a thread of execution, a program, integrated circuitry, and a computer. A computer component(s) may reside within a process and/or thread. A computer component may be localized on one computer and/or may be distributed between multiple computers.

As used herein the terms "memory" and "data store" are used interchangeably and generally refer to a physical and/or logical entity that can store data. A data store may be, for example, a database, a table, a file, a list, a queue, a heap, a memory, a register, and so on. A data store may reside in one logical and/or physical entity and/or may be distributed between multiple logical and/or physical entities. A memory device may include a random-access memory (RAM), a read-only memory (ROM), an internal or external data storage medium (e.g., hard disk drive). Memory may be "permanent memory" (i.e. memory that is not erased by termination of the electrical supply to a computer or processor) or "non-permanent memory". Computer hard-drive, CD-ROM, floppy disk, portable flash drive and DVD are all examples of permanent memory. Random Access Memory (RAM) is an example of non-permanent memory. A file in permanent memory may be editable and re-writable.

The terms "bit depth" and "color depth" are used interchangeably and refer, as used herein, to the number of bits used to represent each pixel in an image. The terms are used to represent bits per pixel and, at other times including e.g., when an image has multiple color channels, the total number of bits used multiplied by the number of total channels of an image. For example, a typical color image using 8 bits per channel is often referred to as a 24-bit color image (8 bits×3 channels). Color scanners and color digital cameras may produce images at a variety of bit depths, including but not limited to e.g., 24-bit (8 bits×3 channels) images, 36-bit (12 bits×3 channels), 48-bit (16 bit×3 channels) images, etc. Grayscale image capture devices may also produce images at a variety of bit depths, though only in one channel, including but not limited to e.g., 1-bit (monochrome), 2-bit, 3-bit, 4-bit, 5-bit, 6-bit, 7-bit, 8-bit, 10-bit, 12-bit, 14-bit, 16-bit, etc. Individual grayscale images may be combined to generate a multichannel or color image where the resulting bit depth will depend on the bit depth of the individual grayscale images.

The term "image segmentation", as used herein, generally refers to the process of partitioning a digital image into multiple segments (sets of pixels, which in some instances may be referred to as superpixels). Image segmentation may be used to locate or otherwise isolated objects and/or boundaries (lines, curves, etc.) in an image. More precisely, image segmentation is the process of including, excluding or assigning a label to pixels in an image such that pixels included in the image (i.e., not excluded from the image) or with the same label share certain characteristics.

General definitions of digital imaging terms not specifically provided herein may be found in various print and online sources known in the art, including but not limited to the Glossary at the Federal Agencies Digitalization Guidelines Initiative (FADGI) available online at www(dot)digitizationguidelines(dot)gov/glossary/.

DETAILED DESCRIPTION

The present disclosure provides methods for automated slide assessments made in conjunction with digital image-based microscopy. Automated methods of acquiring patient information and specimen information from prepared slides, and digitally linking such information into patient-tagged specimen data, are provided. Also provided are methods that include automatically identifying an optimal area for morphological assessment of a blood smear on a hematological slide, including methods for triggering the analysis of such an area, e.g., using an automated digital image-based hematology system. The present disclosure also provides devices, systems and computer readable media for use in performing processes of the herein described methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, the present disclosure provides methods of automated assessments and/or tracking of slide information in an automated cell morphology analysis system. The instant methods may find use in analysis of patient specimens, e.g., histological and/or hematological specimens, prepared on a slide. In some instances, the methods described herein may be performed using hematological slides prepared from hematological specimens including but not limited to e.g., blood, bone marrow, etc. In some instances, the instant methods may be used in the assessment and/or tracking of blood smear slides.

Slides analyzed according to the methods described herein will generally include, as depicted in FIG. 1, a specimen information area (100) and a specimen area (101). The specimen information area (or in some instances referred to as the sample or patient information area) may include various different types of information including but not limited to e.g., information relevant to the subject from which the sample was derived (e.g., identity, age, gender, etc.), information relevant to the sample (e.g., the type of sample, the date acquired/prepared, the method of collection, etc.), information relevant to the assay by which the sample was prepared, information relevant to the method by which the sample is to be assessed, tracking information, etc. In some instances, the patient information area of a slide may be the area commonly referred to as the "frosted" area of the slide, though such area need not necessarily be "frosted". As will be described in more detail below, the patient information area may include machine-readable information, non-machine-readable information or a combination thereof.

The specimen area of the slide generally refers to the area of the slide to which the specimen or sample is applied. As such, the specimen area of the slide will generally include the entirety of the slide excluding the specimen information area. In processes of histological or hematological staining, a sample or specimen, e.g., as collected from a subject, is first applied to the slide and the sample or specimen may cover a significant portion of, i.e., a majority of, the specimen area of the slide or may be spread or smeared to cover a significant portion of the specimen area of the slide.

Figure 2:
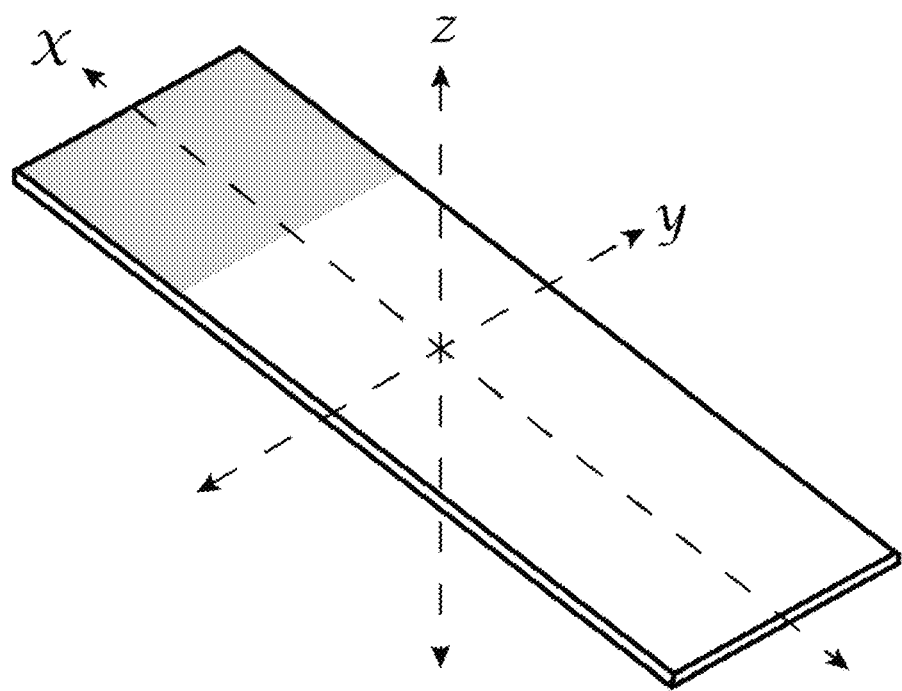
FIG. 2 depicts the axes of a microscope slide as referred to herein.

Slides, as referenced in terms of the instant methods, will be referred to as having three relevant axes. For example, as depicted in FIG. 2, slides referred to in the present disclosure will have an x-axis and a y-axis that define the plane coincident with the surface to which the specimen is applied. By convention, as used herein, when a slide has a long axis and a short axis, the x-axis will refer to the longer axis. Where the surface to which the specimen is applied is square (i.e., the axes are the same length), the x- and y-axes may be interchangeable. The x-axis will also generally, but not exclusively, refer to the axis along which a hematological specimen is smeared. A hematological specimen may be smeared in either direction along the x-axis, though unless specifically noted otherwise, the herein analyzed slides will refer to those where the specimen is smeared from the portion of the specimen area closest to the patient information area to the end of the slide opposite the patient information area. Thus, generally the smears described herein will be the thickest along the x-axis nearest the patient information and the thinnest along the x-axis nearest the end of the slide opposite the patient information area. Correspondingly, the y-axis of a hematological smear will generally refer to the axis perpendicular to the direction of the smear.

Slides, as described herein, will also have a z-axis orthogonal to the xy-plane (i.e., the specimen surface) of the slide. As used herein, the z-axis may also refer to the optical axis or the optical z-axis along which the specimen is brought into focus when viewed through an objective lens of a microscope.

Hematological smears of the subject disclosure will generally have an optimal area for performing an analysis of the specimen wherein such area is characterized by having cells dispersed in a monolayer and having cell distribution characteristics that are best for automated morphology assessments. As noted above, a hematological smear will generally be thickest near one end of the smear getting progressively thinner towards the opposite end. Thicker areas of the smear will generally have cell distribution characteristics consistent with an overly dense distribution which are suboptimal for automated morphology assessments. The thinnest areas of the smear will generally have cell distribution characteristics consistent with an overly diffuse distribution which are suboptimal for automated morphology assessments. As such, hematological smears analyzed according to the present disclosure will have an optimal area for analysis having optimal cell distribution characteristics. Such an optimal area for automated morphology assessment will be referred to herein as the morphology assessment area.

Figure 3:
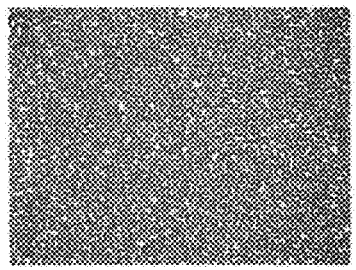
FIG. 3 depicts an example of a thick area of a typical blood smear showing smear characteristics consistent with an overly dense distribution.
Figure 4:
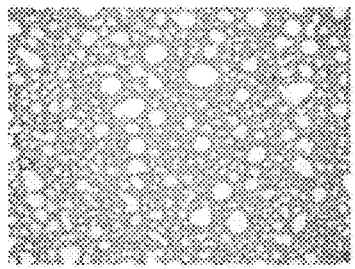
FIG. 4 depicts an example of a thin/feathered area of a typical blood smear showing smear characteristics consistent with an overly diffuse distribution.
Figure 5:
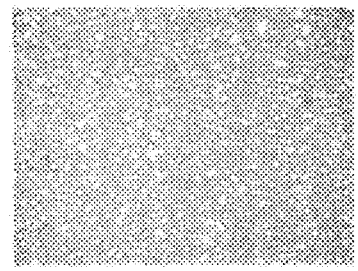
FIG. 5 depicts an example of generally optimal smear distribution characteristics consistent with a morphology assessment area in the monolayer area of a typical blood smear.

Representative images of hematological smears taken at various points along the smear display the characteristics of varied smear thicknesses. For example, as depicted in FIG. 3, an image taken at a relatively thick area of a typical blood smear, the cells of the smear display characteristics consistent with an overly dense distribution. As depicted in FIG. 4, an image taken at a relatively thin/feathered area of a typical blood smear, the cells of the smear display characteristics consistent with an overly diffuse distribution. FIG. 5 demonstrates distribution characteristics that are generally optimal, consistent with a morphology assessment area in the monolayer area of a typical blood smear.

Figure 6:
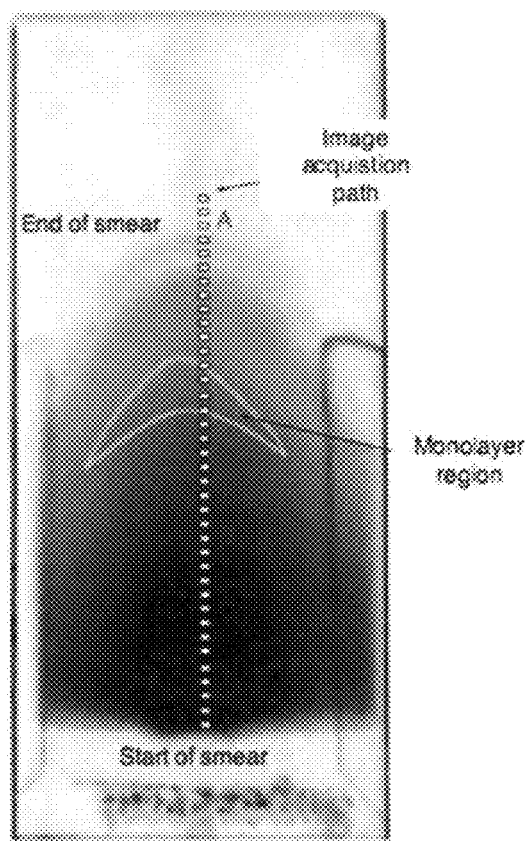
FIG. 6 depicts an example of a morphology assessment area shown relative to the entire blood smear.

An example of a morphology assessment area shown relative to the entire smear is depicted in FIG. 6. As noted in FIG. 6, the smear was performed by spreading the specimen across the x-axis of the slide from the area identified as "start of smear" to the area identified as "end of smear". Accordingly, the smear depicted is thickest near the start and thinnest near the end. An area of the smear where cells are distributed in a monolayer is indicated ("monolayer region"). According to the methods described herein, the monolayer area may be imaged (e.g., along the "image acquisition path" identified) and the acquired images may be analyzed to identify a morphology assessment area within the monolayer area.

Once identified, e.g., according to the methods described herein, the morphology assessment area may be assessed. Assessment of the morphology assessment area will generally involve automated analysis of the morphology of cells within the morphology assessment area to derive values used in cell classification. As an alternative to automated assessments, in some instances, automated identification and imaging of a morphology assessment area may facilitate rapid manual review of the morphology of cells present in the morphology assessment area. Whether performed manually or automatically, the cells analyzed in a morphology assessment will vary and may include e.g., blood cells including e.g., nucleated white blood cells, nucleated red blood cells, enucleated red blood cells, and the like.

Morphology assessments of cells present in the morphology assessment area may include extracting one or more features to provide a calculated value pertaining to one or more cells or one or more portions of a cell. Accordingly, extracted features may pertain to a cell as a whole or various cellular portions including but not limited to cellular portions defined by a structural unit of a cell (i.e., any subcellular component of the cell resolvable through microscopy including e.g., nuclei, cytoplasm, chromatin/heterochromatin, membrane, granules, etc.) or cellular portions defined by some other criteria including non-structural criteria (e.g., criterion based or derived from one or more calculated positions or measures of the cell independent of underlying cellular structure including e.g., the diameter of the cell, the centroid of the cell, the perimeter of the cell, one or more annuli or pallor rings of the cell, etc.). Morphology assessments of cells present in the morphology assessment area may include stain dependent or stain-independent features and feature-based assessments thereof, including but not limited to e.g., those described in U.S. Provisional Patent Application No. 62/269,205, the disclosure of which is incorporated herein by reference in its entirety.

Assessments of the morphology assessment area may involve or may exclude the images captured and used in identifying the morphology assessment area. For example, in some instances, a morphology assessment may derive one or more cellular features used in making an assessment of a subject from an image captured and used in identifying the morphology assessment area. In some instances, a morphology assessment may exclude the image(s) used in identifying the morphology assessment area and cellular features used in making an assessment of a subject may be derived from one or more newly captured images (e.g., a new image scan) of the identified morphology assessment area.

In some instances, once the morphology assessment area is identified, the area may be scanned at a magnification greater than that used in capturing the images used in identifying the morphology assessment area. For example, where the images used in identifying the morphology assessment area are captured using a 10× magnification objective, a subsequent scan of the morphology assessment area may be performed using one or more objectives with a magnification greater than 10× including but not limited to e.g., 20×, 40×, 60× or 100×. Where the images used in identifying the morphology assessment area are captured using a 20× magnification objective, a subsequent scan of the morphology assessment area may be performed using one or more objectives with a magnification greater than 20× including but not limited to e.g., 40×, 60× or 100×.

In some instances, the magnification of the actual image captured may vary from the magnification provided by the objective, including e.g., where the image is captured using a photo tube (i.e., tube lens) having a magnification other than 1× including but not limited to e.g., a 0.5× photo tube, a 1.5× photo tube, a 2× photo tube and the like. Accordingly, the actual magnification of images captured according to the methods described herein, whether captured for identifying the morphology assessment area or captured during assessment, will vary and may range from 5× or less to 200× or more including but not limited to e.g., 5×, 7.5×, 10×, 15×, 20×, 30×, 40×, 50×, 60×, 100×, 120×, 150×, 200×, etc. Assessment of a subject specimen, e.g., following identification of a morphology assessment area, may therefore be performed at essentially any magnification required to capture desired cellular morphological features, e.g., as analyzed to extract cellular features used in various automated specimen assessment procedures, provided the microscopic imaging system is configured with sufficient optical components. Image acquisition, processing and analysis steps, used in the subject methods to identify the morphology assessment area, are described in more detail below.

In addition, the methods of the present disclosure may include, in some instances, methods of specimen tracking, where e.g., the results of a morphology assessment may be ultimately linked to specimen and/or patient information obtained from the slide. In automated morphology assessments specimen tracking can promote properly associating the result of an assessment to a particular subject from which the sample is derived. Without efficient automated specimen tracking, assessment results may be improperly assigned to the wrong subject for various reasons, including e.g., through human error in inputting or assigning patient identification to specimen samples.

Specimen tracking can be achieved, and errors in specimen assignment may be limited, through the use of machine-readable information (also referred to as machine-readable medium or machine-readable medium codes). Non-limiting examples of machine-readable media include but are not limited to e.g., magnetic media such as magnetic disks, cards, tapes, and drums, punched cards and paper tapes, optical disks, barcodes, magnetic ink characters, and the like. In some instances, useful machine-readable codes may include e.g., barcodes including but not limited to e.g., 1 dimensional (1D) barcodes, 2 dimensional (2D) barcodes, and the like. In some instances, a unique machine-readable medium (e.g., a barcode) specific for a patient may be attached to the patient information area of a slide before, during or after a specimen obtained from the subject is applied to the slide such that the unique machine-readable medium is permanently associated with the specimen. In some instances, an automated digital cell morphology analyzer used in assessing the patient specimen is capable of reading the machine-readable medium facilitating automated tracking of the specimen.

In some instances, slides analyzed according to the herein described methods may include non-machine-readable information present in the patient information area of the slide. As used herein, the term "non-machine-readable information" generally refers to any pertinent information related to the specimen that is not readable by a machine. As such, non-machine-readable information will vary greatly and may include hand written information including but not limited to e.g., the patient's name or other patient identifier, the sample type, the sample collection date and/or time, the sample collection location, sample processing information (e.g., stain type, labeling information (e.g., antibody information, probe information, etc.), etc.), and the like. As noted, non-machine-readable information may be present with or without associated machine-readable information.

In some instances, non-machine-readable information present on the slide may provide at least some value in one or more of specimen tracking, patient identification or specimen identification. In some instances, non-machine-readable information present on the slide may be critical in one or more of specimen tracking, patient identification or specimen identification. As such, in some instances, it may be desirable to retain non-machine-readable information associated with a slide. Manual entry of non-machine-readable information into an automated analysis system, as alluded to above, may introduce human error resulting in misattribution of the non-machine-readable information.

In some instances, methods of the present disclosure may include automatically capturing non-machine-readable information present on a slide and linking such information with specimen images and/or specimen assessment results. In some instances, the association of non-machine-readable patient information to an image or other data may be referred to herein as "patient-tagging" and thus the linked non-machine-readable patient information and image(s)/data may be referred to as patient-tagged image(s) or patient-tagged data. Accordingly, in some instances, an image of non-machine-readable patient information that is linked to one or more specimen images and/or specimen data may serve as a "patient tag" providing information related to the patient or specimen including but not limited to e.g., the identity of the patient (e.g., the patient's name or other patient identifier), the type of sample, the sample collection date and/or time, the sample collection location, sample processing information (e.g., stain type, labeling information (e.g., antibody information, probe information, etc.), etc.) or combinations thereof.

Tagging of a patient specimen and/or images acquired from a patient specimen and/or data obtained from images may allow for analysis of the specimen, images or data to be directly associated with a patient allowing e.g., for an automated digital cell morphology analyzer to output a clinical characteristic of the patient upon completion of the analysis, including but not limited to e.g., a diagnosis or prognosis of the patient.

Automated specimen tracking and/or automated assessment methods described herein find use in automated digital cell morphology analyzers. For example, methods of automated specimen tracking may be utilized in tracking a slide that includes non-machine readable information that is processed through an automated digital cell morphology analyzer. Methods of automated identification of a morphology assessment area may be utilized in identifying a morphology assessment area using an automated digital cell morphology analyzer and directing an assessment of the area by an automated digital cell morphology analyzer.

Automated digital cell morphology analyzers will vary and may include but are not limited to e.g., automated hematological analyzers, automated histological analyzers and the like. Such devices are generally capable of capturing digital images of cellular samples and extracting cellular feature data related to the morphology of cells of the sample and/or features of one or more populations of cells of the sample. Images are captured through the use of a microscope component thus allowing imaging and analysis of the cellular features at various magnifications, e.g., as described above. Non-limiting examples of automated digital cell morphology analyzers include automated hematological analyzers including but are not limited to e.g., those commercially available from Abbott Laboratories and/or Abbott Diagnostics (including e.g., the CELL-DYN systems, and the like), from Sysmex (including e.g., the Sysmex DI60, CellaVision DM1200, and the CellaVision DM9600 systems and the like), from MEDICA (including e.g., the EasyCell systems, and the like), from Horiba (including e.g., the Pentra and Micros systems, and the like), from Siemens (including e.g., the ADVIA and Kematek systems, and the like), from Beckman Coulter (including e.g., the UniCel systems, and the like), from Roche Diagnostics (including e.g., the cobas m 511 systems, and the like) etc. Useful digital morphology systems may also include e.g., those described in U.S. Provisional Patent Application No. 62/269,535, the disclosure of which is incorporated herein by reference in its entirety. Automated digital cell morphology analyzers may be configured and/or programmed to perform one or more steps of various processes including but not limited to e.g., image acquisition, processing and analysis as well as one or more physical slide manipulations, including e.g., those of the herein described methods.

Image Acquisition, Processing and Analysis

As noted above, the methods of the present disclosure may include one or more image acquisition, processing and/or analysis steps. Image acquisition, processing and/or analysis steps may be used in identifying a morphology assessment area of a hematological smear. Image acquisition steps may find use in various methods including e.g., the acquisition of one or more images of a patient information area of a slide e.g., as used in specimen tracking methods.

Methods useful in identifying a morphology assessment area of a hematological smear will generally begin at an initial (i.e., starting) xy-position of a slide or smear, which initial xy-positions will vary. For example, an initial xy-position may be chosen relative to the slide (using e.g., the axes set forth in FIG. 2 for reference) and e.g., may be the center of the slide, the center of the specimen area of the slide, etc. In some instances, the starting xy-position may be centered along the y-axis of the slide but off-center along the x-axis including e.g., where the starting position is near the boundary between the patient information area and the specimen area but centered along the y-axis. In some instances, the initial xy-position may be chosen relative to the smear and e.g., may be the center of the smear, a position at the thick end of the smear, a position at the thin end of the smear, etc. In some instances, the initial xy-position may be chosen relative to both the slide and the smear including e.g., where the initial xy-position is centered along the y-axis of the slide and the center of the smear along its x-axis, centered along the y-axis of the slide and at the thick end of the smear, centered along the y-axis of the slide and at the thin end of the smear, etc.

At an initial xy-position the methods may include acquiring a plurality of images along the z-axis of the slide for use in identifying a starting (i.e., initial) z-plane (i.e., z-axis position). In some instances, a plurality of images along the z-axis of the slide may be referred to herein as a plurality of z-axis images. Such images may be acquired along an optical z-axis through various means including but not limited to e.g., by varying the distances between the slide and objective lens and capturing multiple images during such varying. The distances between the slide and objective lens may be varied by any convenient process including but not limited to e.g., through moving the objective lens progressively closer to the slide, by moving the objective lens progressively further from the slide, by moving the slide progressively closer to the objective lens, by moving the slide progressively further from the slide, moving both the slide and the objective lens, etc. The distance between the objective lens and the slide may be varied continuously (i.e., where the moving element(s) (i.e., the lens, slide or both the lens and the slide)) do not pause during the varying or may be varied discontinuously (i.e., where the lens, slide or both the lens and the slide pause during the varying).

In some instances, the distance between the objective lens and the slide may be varied discontinuously where the moving element(s) (i.e., the lens, slide or both the lens and the slide) are moved in a plurality of distinct steps along the z-axis (i.e., distinct z-axis steps). Useful distinct z-axis steps will vary depending on a number of factors including but not limited to e.g., the specimen or smear thickness, the desired optical z-axis resolution, etc., and may range from 0.1 µm or less to 10 µm or more including but not limited to e.g., from 0.1 µm to 10 µm, from 0.5 µm to 10 µm, from 1.0 µm to 10 µm, from 2 µm to 10 µm, from 5 µm to 10 µm, from 0.1 µm to 5 µm, from 0.1 µm to 2 µm, from 0.1 µm to 1.0 µm, from 0.5 µm to 5 µm, from 1 µm to 5 µm, from 2 µm to 5 µm, 0.1 µm, 1.0 µm, 1.5 µm, 2 µm, 3 µm, 4 µm, 5 µm, 6 µm, 7 µm, 8 µm, 9 µm, 10 µm, and the like.

The overall sampled z-axis distance obtained by varying the distance between the objective lens and the slide, regardless of whether varied continuously or discontinuously, may range from 10 µm or less to 300 µm or more including but not limited to e.g., 10 µm to 300 µm, 25 µm to 300 µm, 50 µm to 300 µm, 75 µm to 300 µm, 100 µm to 300 µm, 150 µm to 300 µm, 200 µm to 300 µm, 10 µm to 200 µm, 10 µm to 150 µm, 10 µm to 100 µm, 10 µm to 75 µm, 10 µm to 50 µm, 50 µm to 200 µm, 50 µm to 150 µm, etc. Accordingly, the number of individual z-axis images obtained over the z-axis range may vary and may range from 2 or more but generally not more than 50, including but not limited to e.g., 2 or more, 3 or more, 4 or more, 5 or more, 6 or more, 7 or more, 8 or more, 9 or more, 10 or more, 15 or more, 20 or more, 25 or more, 30 or more, etc.

For a plurality of z-axis images an optimal z-axis image may be selected. In some instances, an optimal z-axis image may be selected from a plurality of z-axis images acquired during a scan of the specimen or a potion thereof, e.g., during the collection of images at a plurality of xy-locations. In some instances, an optimal z-axis image may be selected from a plurality of z-axis images acquired at an initial xy-position. Any convenient method of selecting the optimal z-axis image may be employed including but not limited to by comparing z-axis images captured at a particular xy-position (e.g., an initial xy-position). During comparison of the images of a plurality of z-axis images one or more statistical transformations may be applied to the images to facilitate comparison. Useful statistical transformations include but are not limited to e.g., fast Fourier transform.

An optimal z-axis image selected at an initial xy-location may be utilized as the z-axis starting point, also referred to as the starting focal z-plane, for further imaging of a specimen. In some instances, imaging using a starting focal z-plane as the z-axis starting point for further imaging at subsequent locations may be referred to as imaging "based on the starting focal z-plane". Acquiring a plurality of z-axis images at a particular xy-position based on a starting focal z-plane may include capturing an image at the particular xy-position at the starting focal z-plane and capturing additional images at the xy-position that are one or more predetermined z-axis steps from the starting focal z-plane. For example, a first image at a starting focal z-plane may be captured and two or more additional images at a set z-distance from the starting focal z-plane may be subsequently captured, where e.g., the additional images may be captured above and/or below the starting focal z-plane.

Useful z-distances above/below a starting focal z-plane that may be used in capturing a plurality of z-axis images may vary and may range from 0.1 µm or less to 10 µm or more including but not limited to e.g., from 0.1 µm to 10 µm, from 0.5 µm to 10 µm, from 1.0 µm to 10 µm, from 2 µm to 10 µm, from 5 µm to 10 µm, from 0.1 µm to 5 µm, from 0.1 µm to 2 µm, from 0.1 µm to 1.0 µm, from 0.5 µm to 5 µm, from 1 µm to 5 µm, from 2 µm to 5 µm, 0.1 µm, 1.0 µm, 1.5 µm, 2 µm, 3 µm, 4 µm, 5 µm, 6 µm, 7 µm, 8 µm, 9 µm, 10 µm, and the like.

As a non-limiting example, in some embodiments, the capture of a plurality of z-axis images at multiple xy-positions during a scan of a blood smear specimen may account for changes in the actual optimal focal z-plane during scanning. For example, due to numerous potential variations, e.g., in slide thickness, smear thickness, microscope stage angle, etc., the optimal z-axis for imaging may drift during movement of the slide and/or the objective lens during a scan.

The present methods may include moving the slide and the objective lens relative to one another in a xy-plane, e.g., to facilitate scanning of the slide. A slide may be scanned in a variety of directions relative to the x-axis of the slide, relative to the x-axis of the specimen, relative to the y-axis of the slide, relative to the y-axis of the specimen, diagonal relative to the slide, diagonal relative to the specimen, etc. In some instances, the slide may remain or be held stationary and the objective lens may be moved. In some instances, the objective lens may remain or be held stationary and the slide may be moved. In some instances, both the objective lens and the slide may be moved. Moving the slide and the objective lens relative to one another may involve moving the slide to one or more xy-locations on the slide, including where the moving facilitates moving through a plurality of xy-locations. In some instances, the plurality of xy-locations may be along an axis of the slide, including e.g., along the x-axis of the slide, along the y-axis of the slide, etc. As such, in some instances, the slide or the objective may move in only one dimension relative to the slide such that the position along one axis of the slide remains constant and only the position along the other axis varies, including e.g., where the position along the y-axis remains constant (e.g., the objective stays in the middle of the slide along the y-axis) and the position along the x-axis varies (e.g., the objective scans along the x-axis) or vice versa. Moving of the slide, objective or both may be performed in essentially any manner to facilitate arrival at one or more particular xy-locations of the slide and/or scanning of the slide or specimen to acquire a desired plurality of images at multiple xy-locations.

Moving of the slide and the objective lens relative to one another may be performed in a continuous or discontinuous manner with respect to the imaging performed at the various xy-locations which are scanned. For example, in some instances, the slide and the objective lens may be moved discontinuously relative to one another, e.g., such that the slide, the objective lens or both are moved in distinct steps. The distinct steps through which the slide, objective or both are moved may be in any direction relative to the xy-plane of the slide including but not limited to e.g., distinct x-axis steps, distinct y-axis steps, distinct diagonal steps, etc. The distinct steps may be configured such that successive images are acquired with or without gaps between them. For example, in some instances, images may be captured in distinct x-axis steps such that the movement between steps is greater than the length of the area captured in an image in the relevant axis resulting in a plurality of images of areas of the slide with spatial gaps between them. In some instances, images may be captured in distinct x-axis steps such that the movement between steps is less than the length of the area captured in image in the relevant axis resulting in a plurality of images of areas of the slide with no spatial gaps between them. Images captured with no spatial gaps between them may or may not be at least partially overlapping.

A plurality of images captured along an axis of slide may vary in the total coverage of the specimen imaged. By "total coverage of the specimen imaged" is meant the amount of the specimen or the length of the axis of the specimen that the plurality of the images collectively represents. The amount of an axis covered by a plurality of images may be determined, e.g., by comparing the distance from the first xy-location to the last xy-location of the plurality to the overall length of the axis. For example, in some instances, the amount of a specimen axis (e.g., specimen x-axis) covered by a plurality of images acquired along the specimen axis may be determined by comparing the distance from the first xy-location to the last xy-location of the plurality to the overall length of the specimen axis (e.g., the overall length of a blood smear along its x-axis). The relative length of an imaged axis (e.g., a specimen axis including e.g., the x-axis of a blood smear) covered by a plurality of images will vary and may range from 100% of the length of the axis or less, including but not limited to e.g., 100% of the length of the axis, less than 100% of the length of the axis, less than 75% of the length of the axis, less than 50% of the length of the axis, less than 25% of the length of the axis, between 25% and 100% of the length of the axis, between 50% and 100% of the length of the axis, between 75% and 100% of the length of the axis, between 25% and 75% of the length of the axis, between 50% and 75% of the length of the axis, between 25% and 50% of the length of the axis, more than 25% of the length of the axis, more than 50% of the length of the axis, more than 75% of the length of the axis, and the like.

Accordingly, in some instances, the plurality of images may cover a substantial portion of the length of a blood smear including e.g., where the plurality of images covers 10% or more of the total length of a blood smear including but not limited to e.g., 15% or more, 20% or more, 25% or more, 30% or more, 40% or more, 50% or more, 60% or more, 70% or more, 75% or more, 80% or more, 90% or more, etc.

In some instances, the amount of a specimen covered by a plurality of images may be determined, e.g., by comparing the total area imaged in the plurality of images to the total area covered by the specimen. For example, the total area of the slide covered by the specimen may be calculated and compared to the total area imaged in the combined plurality of images captured at various xy-locations.

At various xy-locations the methods may include acquiring a plurality of images along a z-axis (i.e., a plurality of z-axis images) at each location for use in selecting an optimal z-axis image for each xy-location. Such images may be acquired along an optical z-axis through various means including but not limited to e.g., by varying the distances between the slide and objective lens and capturing multiple images during such varying. The distances between the slide and objective lens may be varied by any convenient process including but not limited to e.g., through moving the objective lens progressively closer to the slide, by moving the objective lens progressively further from the slide, by moving the slide progressively closer to the objective lens, by moving the slide progressively further from the slide, moving both the slide and the objective lens, etc. The distance between the objective lens and the slide may be varied continuously (i.e., where the moving element(s) (i.e., the lens, slide or both the lens and the slide)) do not pause during the varying or may be varied discontinuously (i.e., where the lens, slide or both the lens and the slide pause during the varying).

In some instances, the distance between the objective lens and the slide may be varied discontinuously where the moving element(s) (i.e., the lens, slide or both the lens and the slide) are moved in a plurality of distinct steps along the z-axis (i.e., distinct z-axis steps). Useful distinct z-axis steps will vary depending on a number of factors including but not limited to e.g., the specimen or smear thickness, the desired optical z-axis resolution, etc., and may range from 0.1 µm or less to 10 µm or more including but not limited to e.g., from 0.1 µm to 10 µm, from 0.5 µm to 10 µm, from 1.0 µm to 10 µm, from 2 µm to 10 µm, from 5 µm to 10 µm, from 0.1 µm to 5 µm, from 0.1 µm to 2 µm, from 0.1 µm to 1.0 µm, from 0.5 µm to 5 µm, from 1 µm to 5 µm, from 2 µm to 5 µm, 0.1 µm, 1.0 µm, 1.5 µm, 2 µm, 3 µm, 4 µm, 5 µm, 6 µm, 7 µm, 8 µm, 9 µm, 10 µm, and the like.

The images of the acquired plurality of images along a z-axis at each xy-location may be compared to select an optimal z-axis image for each xy-location. As described above, any convenient method of selecting an optimal z-axis image may be employed including but not limited to comparisons employing one or more statistical transformations applied to the images, including but not limited to e.g., fast Fourier transform.

Images captured at a plurality of xy-locations, including e.g., optimal z-axis images captured at each xy-location, may be analyzed to extract one or more features representative of the xy-location. For example, in some instances, one or more density distribution features may be analyzed and one or more density distribution feature values be extracted. The entire image may be analyzed or a portion of the image may be analyzed including e.g., where a region of interest (ROI) of the image is analyzed.

ROIs of an image may be any collection of pixels useful for extracting one or more features representative of the xy-location and, e.g., deriving a density distribution feature value for use in the methods as described herein. A single ROI or multiple ROIs may be defined for a particular image and, e.g., a ROI may include the entire image or essentially the entire image or a portion thereof. ROIs that include less than the entire image may be defined based on any convenient parameters. For example, useful ROIs may include a portion of the images, of any shape, taken from any area of the image including e.g., the center of the image, an off-center area of the image, an edge or the image, etc. Correspondingly, an ROI may include any portion of an image of 100% or less of the image, including but not limited to e.g., 100% of the image, between 1% and 99% of the image, between 50% and 100% of the image, between 1% and 50% of the image, between 10% and 90% of the image, between 20% and 80% of the image, between 30% and 70% of the image, less than 90% of the image, less than 80% of the image, less than 70% of the image, less than 60% of the image, less than 50% of the image, more than 50% of the image, more than 60% of the image, more than 70% of the image, more than 80% of the image, more than 90% of the image, etc. In some instances, an ROI of an image may include the remaining portion of an image when one or more edges of an image are cropped, e.g., to remove aberrations or inconsistencies of the image associated with image edges and/or corners including e.g., edge shading or darkened corners.

Where multiple ROIs are obtained, e.g., from a single image, over multiple steps of a method, during an iterative analysis, etc., successive ROIs may be held constant or may be varied, e.g., the size of the ROIs may be varied. For example, in some instances, multiple ROIs (i.e., a plurality of ROIs) may be analyzed from multiple images where each ROI of the plurality represent essentially the same portion of each image from which is obtained. In some instances, multiple ROIs (i.e., a plurality of ROIs) may be analyzed from multiple images where at least some of the ROIs of the plurality represent different portions of the images from which they are obtained. In some instances, multiple ROIs may be rectangular, having an x-axis and a y-axis and the size of the ROIs may be varied such that the ROIs of varied size remain rectangular including where, e.g., the x-axis and the y-axis of the ROI are varied equally or the x-axis and the y-axis of the ROI are varied unequally. Correspondingly, in some instances, the shape of multiple rectangular ROIs may be varied or held constant including e.g., where the shape of successively analyzed ROIs are essentially the same shape or dimensions or a different shape or dimensions as compared to the image from which they were obtained.

The analyzing performed, e.g., to extract one or more density distribution feature values, will vary and may include where the density distribution feature is or is not based on a color feature of the image. As such, density distribution feature values may be color feature values or non-color feature values. Color feature values will generally depend on image information extracted from one or more color channels of the image which is influenced by the color staining of the specimen. Non-color feature values may be derived from image information extracted from the overall image or a portion thereof regardless of color mode (e.g., color, grayscale, binary, etc.) of the image, or one or more color channels, but is generally not influenced by any color staining of the specimen.

Density distribution feature values extracted from density distribution features will be indicative, either alone or in combination, of the density distribution of cells of the specimen and/or whether the image or ROI analyzed contains a morphology assessment area. Accordingly, one or more morphology assessment area(s) of a specimen may be identified based on one or more extracted density distribution feature values. Accordingly, density distribution features analyzed in the subject methods will include those density distribution features that may be automatically extracted from digital images and analyzed to identify one or more morphology assessment area(s) of a specimen that can be used in an assessment performed by an automated digital cell morphology analyzer. Where combinations of multiple density distribution feature values are employed useful numbers of individual density distribution feature values of such combinations will vary and may range from 2 to 20 or more, including but not limited to 2 or more, 3 or more, 4 or more, 5 or more, 6 or more, 7 or more, 8 or more, 9 or more, 10 or more, 15 or more, 2 to 20, 3 to 20, 4 to 20, 5 to 20, 6 to 20, 7 to 20, 8 to 20, 2 to 15, 3 to 15, 4 to 15, 5 to 15, 6 to 15, 7 to 15, 8 to 15, 2 to 10, 3 to 10, 4 to 10, 5 to 10, 6 to 10, 7 to 10, 8 to 10, 2 to 9, 2 to 8, 2 to 7, 2 to 6, 2 to 5, 2 to 4, etc. Combinations of multiple density distribution feature values may include those derived exclusively from non-color features, exclusively from color features, or a combination of color and non-color features.

Useful density distribution features of a specimen will vary and may include but are not limited to e.g., the density of cells within an image or an ROI, the variation in the density of cells within an image or ROI, the variation in the density of cells between images or ROIs, the size of cells within an image or an ROI, the variation in the size of cells within an image or ROI, the variation in the size of cells between images or ROIs, the shape of cells within an image or an ROI, the variation in the shape of cells within an image or ROI, the variation in the shape of cells between images or ROIs, the pallor of cells within an image or an ROI, the variation in the pallor of cells within an image or ROI, the variation in the pallor of cells between images or ROIs, the color of cells within an image or an ROI, the variation in the color of cells within an image or ROI, the variation in the color of cells between images or ROIs, the number of overlapping cells within an image or an ROI, and combinations thereof. Accordingly, useful density distribution features include but are not limited to e.g., a cell count, a coefficient of variation (CV) index for a cell count, a cell size, a CV index for a cell size, an index defining a cell shape, a CV for an index for a cell shape, an index defining central pallor of the cell, an index defining cell color, a count of overlapping cells, and combinations thereof.

Extracting density distribution feature values from an image or a ROI, according to the subject methods, may include one more image processing steps which may employ one or more image processing algorithms. Useful image processing steps may include but are not limited to e.g., splitting channels of a multichannel image, generating one or more image masks (e.g., a foreground mask, a color mask, a threshold mask, a combined mask (e.g., a combined color and foreground mask), etc.), space filing or hole closing (e.g., hole closing in a generated mask), noise filtering, segmentation (e.g., cell segmentation), and the like.

Image processing steps generally include the processing of digital images, which may vary and may be in binary (e.g., black and white), grayscale or color formats. Images of various formats may further be converted between formats, as desired, by suitable image processing algorithms. For example, a color image may be "split" into individual color channels to produce individual grayscale images for each color channel. For example, a red, green and blue image (RGB) image may be split into individual red, green and blue channels to produce a grayscale image of the red channel, a grayscale image of the green channel and a grayscale image of the blue channel. Color images may be converted between color spaces and split into any convenient and appropriate color channels of a particular color space including but not limited to e.g., RGB color space, CMYK color space, HSV color space, CIE color space, Lab color space, CIELUV color space, YCbCr color space, and the like. Binary images and grayscale images may be applied to a channel of a color image and, e.g., where multiple binary or grayscale images are applied to multiple channels of a color image, a color image may be constructed, or "merged", from binary and/or grayscale images. Where a color image is split into individual color channels to produce grayscale images, an individual grayscale image may be referred to by its prior channel designation, e.g., a grayscale image produced from the red channel may be referred to as "red" in subsequent steps and/or any values generated from the "red" channel may be referred to by their prior channel designation, e.g., the mean "red" intensities refers to the mean intensity values derived from the grayscale image produced from the red channel. Images and values derived from other color spaces may be referred to using corresponding nomenclature.

Accordingly, digital color images may be processed as color images (i.e., as multichannel images) or may be converted or split into two or more individual color channels prior to processing. When split into two or more individual color channels, any number of the resulting split images may be used in further processing steps including but not limited to all the split images (i.e., all the individual channels of the image) or only one of the split images (i.e., only one of the individual channels of the image) or one or more, including but not limited to two or more, three or more, two, three, etc. of the split images (i.e., the individual channels of the image).

Digital color or monochrome images may be segmented prior to processing. As used herein, the terms "segmented" and "segmentation" as they relate to image processing generally refer to the division or partitioning of an image into meaningful structures or segments. Various methods for image segmentation may find use in the methods described herein or in preparation of an image for processing according to the methods as described herein. Selection of a particular segmentation method or combination of segmentation methods will depend on various factors including the type of image captured, the nature of subject matter of the image, the desired result of the image processing, the color or monochrome features used, the desired density distribution feature value(s) to be extracted, etc.

In some instances, image segmentation may make use of one or more of threshold based segmentation, edge based segmentation and region based segmentation. Specific image segmentation methods include but are not limited to thresholding methods, clustering methods, compression-based methods, histogram-based methods, edge detection methods, dual clustering methods, region-growing methods, partial differential equation-based methods (e.g., parametric methods, level set methods, fast marching methods, etc.), variational methods, graph partitioning methods (e.g., Markov Random Fields methods), watershed transformation methods, model based segmentation methods, multi-scale segmentation methods, semi-automatic segmentation methods, trainable segmentation methods, and the like.

Other digital image processing image transformations that may find use in the described methods include but are not limited to e.g., point processing transformations (e.g., negative transform, log transform, inverse log transform, nth root transform, nth power transform, gamma correction, contrast transforms (e.g., contrast stretching), window center correction, histogram equalization, etc.), filtering (i.e., neighbor) transformations (e.g., mean filters, Gaussian filters, median filters, image gradient filters, Laplacian filters, normalized cross correlation (NCC) filters, etc.), and the like.

In some instances, in further image processing steps, e.g., following image segmentation, image transformation, etc., an image mask may be generated. As used herein the terms "mask", as related to image processing, and "image mask" collectively refer to spatial filtering of a digital image so as to limit further processing steps to a defined subset or defined portion of the original image. The defined portion of the digital image, i.e., the mask, may be based on various image-based criteria including but not limited to local or relative intensity, local or relative color, etc., of pixels or groups of pixels. For example, in some instances, a digital image may be processed (e.g. segmented) to identify one or more groups of pixels and an image mask may be generated based on the identified pixels, or groups thereof, such that further image processing or analysis steps are limited only to those pixels contained within the mask. Various masks may be generated depending on the particular processes to be performed. In some instances, an image mask may involve discarding the image information not contained within the mask (e.g., discarding information associated with a background mask, discarding information of a particular color, discarding information above a particular intensity, discarding information below a particular intensity, etc.) or only further processing or analyzing image information contained within the mask (e.g., only processing or analyzing information associated with a foreground mask, processing or analyzing information associated with a particular color, processing or analyzing information above a particular intensity, processing or analyzing information below a particular intensity, etc.). In some instances, a new image is produced from an image mask containing only the information contained within the mask or excluding information contained within the mask.

In some instances, a digital image may be segmented or a mask may be generated identifying the foreground of the image. Herein the term "foreground" is used consistent with its meaning in the field of digital image processing and generally refers to one or more objects of interest in the image. For example, foreground segmentation of the instant methods may include identifying and/or segmenting the cells of the image from the background of the image. Foreground segmentation may be applied to any starting image including but not limited to unprocessed color images or split color channels. In some instances, a foreground segmentation may be applied to a split color channel including e.g., where the red channel is foreground segmented, the green channel is foreground segmented or the blue channel is foreground segmented. In some instances, foreground segmentation may be performed based on the relative image intensities of objects of interest as compared to elements of the image that are not of interest, including e.g., the background. A foreground mask may limit a further image processing or analysis step to only those pixels contained within the foreground mask.

In some instances, a digital image may be segmented or a mask may be generated according to cellular boundaries and the cellular boundaries may be the basis for further processing or analysis. In some instances, an ROI may comprise all of the segmented cells of the image or a subset of the segmented cells of the image, e.g., based on some criteria including but not limited to e.g., size, shape, brightness, color, etc. In some instances an ROI based on or comprising segmented cells may serve as the basis for generating a cellular mask that contains all or a portion of the segmented cells. A cellular mask may limit a further image processing or analysis step to only those pixels contained within the cellular mask and/or only those cellular structures contained within the cellular mask.

Following generation of a mask, including but not limited to e.g., a foreground mask or a cellular mask, the generated mask may be modified. Modification of generated masks may be applied for various reasons including but not limited to e.g., the presence of noise in the mask, the presence of one or more holes in the mask. For example, in some instances, a mask generated for cells having inconsistent image intensity across the cell may, based on the particular masking parameters utilized, result in a mask that includes the perimeters of the cells but excludes the centers of the cells. In some instances, such excluded centers of cells of interest in a subject mask may be referred to as "holes". As such, in some instances, methods of the present disclosure may include a step of closing one or more holes in a generated mask, including e.g., to include the image information associated with the holes in further image processing and/or analysis steps (e.g., include the image information associated with the entire cells of interest).

In some instances, a hole closing algorithm may be used. Useful hole closing algorithms will vary and may be based on a variety of factors including but not limited to e.g., the size of the holes, the relative size of the foreground, the relative size of the background, the relative size of a generated mask, etc. In some instances, a hole closing algorithm may be based on the ratio of the size of the foreground mask to the overall size of the image (referred to herein as the "foreground ratio"), where such ratio may range from 0% to 100% including e.g., from 0% to 19%, from 20% to 59%, from 60% to 79%, from 80% to 100%, etc. In some instances, the hole closing size may be based on the foreground ratio, including e.g., where the hole closing size (e.g. in pixels) is 80 pixels for a ratio from 0% to 19%, 60 pixels for a ratio from 20% to 59%, 40 pixels for a ratio from 60% to 79%, 30 pixels for a ratio from 80% to 100%, etc.

As noted above, image processing may include one or more noise filtering steps. Useful noise filtering steps will vary and may include but are not limited to removing objects from an image or mask that are too large to represent cells, removing objects from an image or mask that are too small to represent cells, and the like. In some instances, joined or overlapping objects, including objects of interest such as cells, may be removed or separated, e.g., through one or more image processing steps including but not limited to e.g., a watershed algorithm.

Following one or more image processing steps, when performed, one or more density distribution feature values may be extracted from the image. In some instances, extraction of the density distribution feature values may be limited to an ROI. In some instances, a mask, e.g., generated as described above, may be applied to the image and the density distribution feature values may be based on the applied mask. Where multiple density distribution feature values are employed in making an assessment, the density distribution feature values used need not necessarily all be extracted from an image having undergone the same image processing steps. For example, in some instances, a first density distribution feature value may be extracted from an unprocessed image and a second density distribution feature value may be extracted from the same image having undergone one or more image processing steps or having had one or more masks applied. In some instances, a first density distribution feature value may be extracted based on one or one set of image processing steps and a second density distribution feature value may be extracted based on a second or a second set of image processing steps. In some instances, two density distribution feature values may be extracted from the same image with the same image processing steps and/or masks applied.

Once extracted, density distribution feature values may be compared. In some instances, a density distribution feature value extracted for a first image may be directly compared to a corresponding density distribution feature value extracted for a second image. In some instances, a set of density distribution feature values extracted for a first image may be directly compared to a corresponding set of density distribution feature values extracted for a second image. Such comparisons may find use in identifying which image, and correspondingly which area of the specimen that corresponds to the image, is associated with density distribution feature values indicative of a morphology assessment area. In some instances, the comparison identifies the density distribution feature value(s) that are more or most closely associated with those indicative of a morphology assessment area. In some instances, the comparison identifies the density distribution feature value(s) that are above a minimum threshold to be indicative of a morphology assessment area. As such, comparisons between density distribution feature values will not be limited to direct, i.e., one-to-one, comparisons and may also include e.g., comparisons to a minimum or maximum threshold or reference value indicative of a morphology assessment area, comparisons to a range indicative of a morphology assessment area, comparisons to a minimum or maximum threshold or reference value indicating that the area is not a morphology assessment area (i.e., an exclusion threshold), comparisons to a range indicating that the area is not a morphology assessment area. In some instances, extracted density distribution feature values may be ranked thereby generating an associated ranking of the imaged areas associated with each distribution feature value. Such rankings may identify the area most likely to be a morphology assessment area, the next most likely morphology assessment area, and so on. Alternatively, such rankings may identify the area least likely to be a morphology assessment area, the next least likely morphology assessment area, and so on.

In some instances, a threshold for a particular extracted density distribution feature value may be employed as a minimum cutoff or quality checkpoint. For example, in some instances, an extracted density distribution feature value may be compared to a reference value prior to or following further processing or assessment, e.g., to determine whether the specimen is of sufficient quality for assessment. In some instances, an initial extracted density distribution feature value may serve as a minimum cutoff or quality checkpoint to be used in determining whether further assessment to identify a morphology assessment area is warranted. In some instances, following identification of a morphology assessment an extracted density distribution feature value may serve as a minimum cutoff or quality checkpoint to be used in determining whether further assessment of the specimen, e.g., a clinical analysis of the specimen, is warranted. Extracted density distribution feature value that may be useful as such a minimum cutoff or quality checkpoint will vary and may include e.g., an initial cell count or any of the herein described density distribution feature values. For example, in some instances, an initial cell count density distribution feature value may be assessed relative to a reference threshold to determine if further assessment of the specimen is warranted.

Images utilized in the herein described methods will be digital images, the types and acquisition of which may vary. A "digital image", as used herein, generally refers to a numeric representation (e.g., binary representation) of a two-dimensional image that may be of fixed or unfixed resolution. Fixed resolution images have a fixed number of rows and columns of pixels in an XY orientation. In some instances, digital images may be three-dimensional having fixed number of voxels in a XYZ orientation. Pixels and voxels are stored in computer memory as a raster image or raster map, a two-dimensional or three-dimensional array of small integers transmitted or stored in an uncompressed or compressed form. Suitable digital image file formats include but are not limited to e.g., BMP, BPG, CD5, DEEP, ECW, Exif, FITS, FLIF, GIF, HDR, HEIF, ILBM, ILBM, IMG, IMG, JPEG 2000, JPEG XR, JPEG/JFIF, Layered Image File Format, Nrrd, PAM, PBM, PCX, PGF, PGM, PLBM, PNG, PNM, PPM, SGI, SID, Sun Raster, TGA, TIFF, VICAR, WEBP, and the like.

Digital images may be a variety of image bit depths depending, e.g., on the particular type of image captured (e.g., color or grayscale) and the sensitivity of the digital camera or other image capture device and may include but are not limited to e.g., 8-bit, 10-bit, 12-bit, 14-bit, 16-bit, 18-bit, 24-bit, 30-bit, 36-bit, 48-bit, 64-bit, and the like. In some instances, the channels of a color image may individually be or may be split into individual 8-bit grayscale images. In some instances, the channels of a color image may individually be or may be split into individual 16-bit grayscale images. In some instances, a digital color image may be generated from multiple individually captured grayscale images that are combined into a single image by assigning the individually captured grayscale images to different color channels of the single image. In other instances, all the colors of a digital color image are captures simultaneously, e.g., through the use of an image capture device having multiple photo detectors assigned to different colors and one or more optical devices for directing light of different colors to different photo detectors.

Aspects of the disclosed methods include obtaining a digital image (e.g., a digital color image or a digital monochrome image) of biological specimen applied to a slide. Such obtaining may include transfer to of the digital image to image processing circuitry or newly obtaining the image, e.g., by capturing a digital image of a prepared specimen on a slide with a suitable image capture device, described in more detail below. As such, obtaining a digital image of specimen as described herein may include receiving a digital image including e.g., where the digital image is received from various sources including but not limited to an integrated imaging device, an external imaging device, a computer memory, a computer readable medium, a server, a remote server, etc. Digital images may be received by a data or computer connection or may be received on a computer readable medium.

In addition to image acquisition of the specimen area, e.g., related to extraction of density distribution feature values as described above, the instant methods may also include, in some instances, acquiring a digital image of the patient information area of the slide. Such acquired images of the patient information area of the slide may include visible specimen information that may or may not be machine-readable or may include both machine-readable and non-machine-readable visible specimen information. As noted above, images of the specimen information area of a slide may find use in generating patient-tagged specimen images and/or patient-tagged specimen data. For example, in some instances, images of the morphology assessment area of a slide may be digitally linked to images of the patient information area to generate patient-tagged morphology assessment area images. In some instances, data extracted from the morphology assessment area may be digitally linked to images of the patient information area to generate patient-tagged morphology assessment area data.

The herein described methods may include storing digital information, including digital images and/or data extracted from digital images. Such digital information may be stored in any convenient manner including but not limited to storing the information in a computer memory and/or on one or more computer readable mediums. For example, digital images, processed or unprocessed, may be routed from an image capture device through a wired or wireless data connection to a computer memory or computer processor configured to write the data to computer memory or other computer readable medium. In some instances, data extracted from one or more digital images, processed or unprocessed, may be routed from an image capture device through a wired or wireless data connection to a computer memory or computer processor configured to write the data to computer memory or other computer readable medium.

Stored images and/or data may be subsequently accessed for various purposes including but not limited to e.g., make a comparison between one or more images, direct or inform the acquisition or analysis of further images (e.g., direct or inform the further acquisition or analysis of an identified morphology assessment area), analysis of a ROI of the image, extract one or more image feature values (e.g., one or more density distribution feature values), make one or more specimen assessments, review of visible machine-readable patient information, review of visible non-machine-readable patient information, and the like. In some instances, where images and/or data is patient-tagged the patient-tag may remain associated with the image and/or data through further steps including e.g., processing, storage, retrieval, etc. In some instances, a patient-tag associated with a first image or datum may be reapplied to further images of the specimen acquired based on the first tagged image or datum. In some instances, a patient-tag associated with a first image or data set may be reapplied to further data extracted from the first image or data set. Such secondary applications of a patient-tag derived from the patient information area of a slide may be likewise stored in a computer memory or other computer readable medium.

Physical Slide Manipulations

As summarized above, methods of the present disclosure may include one or more physical slide manipulations of a slide. By "physical slide manipulations" is generally meant the moving of the slide relative to one or more components of an automated slide analyzer. In some instances, a slide may be moved, i.e., transported, within an automated slide analyzer from one component of the analyzer to another. In some instances, a slide may be moved on or about a particular component of an automated slide analyzer while remaining in contact or otherwise associated with the component (e.g., an imaging stage). Accordingly, physical slide manipulations of the present methods may vary greatly.

As described above, in some instances, a slide may be physically manipulated relative to an objective lens and/or the imaging stage of microscope elements of an automated slide analyzer. For example, a slide may be moved such that an objective lens of the system scans the slide or a portion of the slide, such as along one or more particular axes of the slide as described above. Any convenient means of scanning a slide may be employed including e.g., where an imaging stage with which the slide is in contact is moved relative to the objective lens or the slide itself is moved relative to the objective lens (e.g., in the absence of an imaging stage). In some instances, the slide may be held stationary, with or without an imaging stage, and the objective lens may be moved relative to the slide, e.g., in a scanning motion along one or more axes of the slide or a specimen present on the slide.

As noted above, physical slide manipulations may also include transporting the slide through an automated slide analyzer, e.g., from a first component of the slide analyzer to a second component. For example, in some instances, a slide may be transported to or from an imaging component of the slide analyzer including e.g., to an imaging stage or other imaging area where, e.g., the specimen area of the slide is imaged by one or more imaging objective lenses. In some instances, a slide may be transported from a component of the automated slide analyzer to an area where the slide is imaged. In some instances, the slide may be transported from an area where the slide is imaged to another component of the automated slide analyzer.

Components of an automated slide analyzer from which or to which a slide may be transported will vary and may include e.g., components used in the loading of pre-prepared slides, components used in the preparation of slides for analysis (e.g., specimen application components, slide smearing components, slide staining components, slide drying components, etc.), components used in the storing of slides (e.g., components used in the storing prepared slides either before or after imaging), components used in the disposal of slides (e.g., waste collection areas and devices, waste transport components, etc.), and the like. Such components may include but are not limited to e.g., components of morphology analyzers, including e.g., those automated hematological morphology analyzers described herein.

Transporting a slide through an automated slide analyzer will generally involve moving the slide along a path, where such a path may be entirely or partially within the slide analyzer. A path taken by a slide within a slide analyzer may be defined at its ends by the component form which the slide is transported from to the component to which the slide is transported. Such paths will vary greatly in trajectory and may be straight, arced or include one or more turns. The path a slide takes will depend at least in part on the slide transportation mechanism, herein referred to as a slide conveyor, which will likewise vary greatly, as described in more detail below.

In some instances, a slide may be transported individually through a slide analysis system. For example, a robotic arm or conveyor belt may be employed to transport individual slides through an analysis system and/or perform one or more physical slide manipulations described herein. In some instances, multiple slides may be transported together through a slide analysis system, e.g., as contained collectively in a slide carrier or other device capable of holding a plurality of slides. The path of the slide may be defined by the movement of the slide conveyor regardless of the particular conveyor employed, e.g., robotic arm, conveyor belt, slide carrier, and the like.

In some instances, components between which a slide is transported may be separated between two subsystems of the device such that the method includes transporting the slide between subsystems. Separated subsystems may be next to or above and below one another, requiring transporting the slide horizontally or vertically, respectively. In one example, the method may include preparing slides in an upper level of the system (i.e., an upper subsystem) and imaging and/or analyzing cell morphology in a lower level of the system (i.e., a lower subsystem) such that slides prepared on the upper level are transported to the lower level. Such transporting may be achieved by various means including but not limited to e.g., the use of a slide elevator assembly, as described in more detail below.

During transporting of a slide in or by a slide conveyor the physical orientation of the slide may be manipulated. Essentially and physical manipulation of slide orientation may be performed, e.g., as required by the orientation and/or relative positioning of components of the device relative to one another. For example, in some instances, slides may be rotated. Useful rotational manipulations may include end-to-end or side-to-side rotations. In some instances, a slide may be rotated from a vertical orientation to a horizontal orientation. In some instances, a slide may be rotated from a horizontal orientation to a vertical orientation. Any useful combination of individual orientation manipulations may also be employed.

As one example, in some instances, preparation of a slide may be performed in a vertical orientation. Histological and hematological slides are often stained in a vertical orientation, e.g., lowered into a slide staining bath. Conversely, imaging of histological and hematological slides is often, but not necessarily, performed with the slide in a horizontal orientation. In some instances, one or more slides may be rotated from a vertical orientation, e.g., as oriented during staining, to a horizontal orientation, e.g., for imaging.

While imaging of the specimen area of a slide may generally be performed at a specimen imaging area of the device (e.g., an area containing a digital microscope and associated components) imaging of the patient information area of a slide, where performed, may take place at the specimen imaging area or essentially any other area of the device or along any path of the slide through the device, e.g., during the transport of the slide within the device. Accordingly, imaging of the patient information area may be performed before, during or after transport of the slide, e.g., in or on a slide conveyor, to or from any component of the device, including e.g., any of those components described above.

Imaging of the patient information area of a slide may be performed while the slide is in essentially any orientation. For example, in some instances, an image of the patient information area is acquired when the slide is in a vertical orientation. In some instances, an image of the patient information area is acquired when the slide is in a horizontal orientation. In some instances, imaging of a patient information area may take place before, during or after a physical manipulation of the one or more slides, including e.g., before, during or after a change in orientation of the slide, e.g., before, during or after a change in orientation of the slide from vertical to horizontal, horizontal to vertical, or both.

Depending on the context, imaging may be performed while the slide is moving or stationary. For example, imaging of the specimen area of a slide may generally, but need not necessarily, be performed while the slide is stationary. However, when a slide is scanned for example, imaging may be performed while a slide is being moved or a movement of the slide may include one or more pauses in movement, e.g., to allow capture of an image while the slide is paused. Similarly, capturing an image of the patient information area of a slide may be performed while the slide is moving, e.g., in transport within the device, or stationary, e.g., not during transport or during one or more pauses in transport.

The methods described above may, in some instances, employ or be performed by or otherwise make use of or be associated with one or more of the devices, systems and/or components thereof described below.

Devices and Systems

As summarized above, the present disclosure includes devices, systems and/or components thereof for use in performing processes of the methods described above. The above described methods generally relate to automated slide assessments made in conjunction with digital microscopy utilizing an automated slide analyzer. Automated slide analyzers will vary and will generally include an imaging component and one or more slide handling components. Such systems may or may not include slide preparation components, such as e.g., slide making components, slide staining components, or a combination thereof, such as e.g., the slide maker staining system described below. Automated slide analyzers may be employed to make automated assessments of slides, e.g., histology slides, hematology slides, and the like. Such systems may assess cell morphology and, as such, the present systems include morphology analyzers including but not limited to, e.g., automated hematological morphology analyzers.

Automated hematological morphology analyzers will vary and may include but are not limited to e.g., those available from Abbott Laboratories and/or Abbott Diagnostics (including e.g., the CELL-DYN systems, and the like), from Sysmex (including e.g., the Sysmex DI60, CellaVision DM1200, and the CellaVision DM9600 systems and the like), from MEDICA (including e.g., the EasyCell systems, and the like), from Horiba (including e.g., the Pentra and Micros systems, and the like), from Siemens (including e.g., the ADVIA and Kematek systems, and the like), from Beckman Coulter (including e.g., the UniCel systems, and the like), from Roche Diagnostics (including e.g., the cobas m 511 systems, and the like) etc.

Systems within which the herein described methods may be performed will generally include at least one digital imager. Digital imagers of the subject devices may be configured for imaging of the specimen area of a slide, the patient information area of a slide or both. A digital imager for use in imaging the specimen area of a slide may, in some instances, have different requirements as compared to an imager for use in imaging the patient information area of a slide. For example, an imager for use in imaging of the specimen area of a slide may require greater magnification and higher optical resolution than an imager for use in imaging the patient information area of a slide. Depending on the context, an imager for use in imaging of the specimen area of a slide may require color acquisition capabilities whereas an imager for use in imaging the patient information area of a slide may not. Similarly, a digital imager for use in imaging the patient information area of a slide may, in some instances, have different requirements as compared to an imager for use in imaging the specimen area of a slide. For example, a digital imager for use in imaging the patient information area of a slide may require more rapid image capture as compared to as compared to an imager for use in imaging the specimen area of a slide. In some instances, a single digital imager may suffice for both specimen imaging and patient information area imaging. In some instances, a system or device of the present disclosure may include a plurality of digital imagers including e.g., at least one digital imager configured specifically for imaging the specimen area of a slide and at least one digital imager configured specifically for imaging the patient information area of the slide.

A digital image capture device (i.e., digital imager) of the systems of the present disclosure, depending on the context, may acquire color or monochrome (e.g., grayscale) images. Acquired digital color or monochrome images may be captured using any suitable color or monochrome enabled image capturing device. Suitable digital color or monochrome image capturing devices will be stand-alone image capture units or may be an integrated image capturing device that is part of a larger analysis system including e.g., a histology analyzer, an automated microscopy system, a hematology analyzer, a cytology analyzer, an imaging microfluidics system, etc. Suitable digital color or monochrome image capturing devices will vary greatly depending on the particular imaging context, the purposes of image capture and the associated components of the device or system as a whole.

At a minimum a suitable color or monochrome image capturing device, for use in the described methods, will include a digital color or monochrome camera capable of capturing a digital color or monochrome image and a means of storing the digital color or monochrome image and/or transferring the image to attached image processing circuitry or to an attached storage device for later transfer to image processing circuitry. Suitable digital color or monochrome cameras will vary and will generally include any digital color or monochrome camera with sufficiently high resolution and sufficient color or monochrome capture to capture an image that may be processed according to the methods described herein.

Depending on the particular features used in a subject methods or systems suitable digital cameras may include monochrome or color camera with resolution ranging from less than about 0.3 megapixel to about 14.0 megapixel or more including but not limited to e.g., 0.3 megapixel or more, 0.9 megapixel or more, 1.3 megapixel or more, 1.4 megapixel or more, 2 megapixel or more, 3 megapixel or more, 3.3 megapixel or more, 5 megapixel or more, 7 megapixel or more, 10 megapixel or more, 12 megapixel or more, 14.0 megapixel or more, and the like.

Suitable digital cameras include but are not limited to e.g., custom build digital cameras, consumer grade digital cameras (e.g., consumer grade digital cameras converted for microscopic use) and those digital microscopy cameras commercially available from various manufactures including but not limited to e.g., Dino-Eye, Dino-Lite, Jenoptik ProgRes, KoPa, Leica, Motic, Olympus, Omano, OptixCam, PixelLINK, Zeiss, etc. In some instances, a high speed (i.e., fast acquisition) camera may be employed, e.g., for capture of images of the patient information area of a slide.

In some instances, a digital camera of the instant system may be attached to a microscope configured for manual or automated microscopy. Any suitable microscope may find use in the described systems provided the microscope is configured with sufficient optics and provides sufficient magnification to allow the capture of digital images that can be processed according to the methods described herein. As such, microscope components of the instant systems include custom units, e.g., as assembled from individual microscope components and commercially available units.

Suitable microscopes include but are not limited to e.g., those available from various manufactures including e.g., Bruker Optics (www(dot)brukeroptics(dot)com), Carl Zeiss (www(dot)zeiss(dot)com), CRAIC (www(dot)microspectra (dot)com), Edmund Optics (www(dot)edmundoptics(dot) com), FEI (www(dot)fei(dot)com), Hamamatsu (www(dot) hamamatsu(dot)com), Hirox-USA (www(dot)hirox-usa(dot) com), Hitachi High Technologies (www(dot)hitachi-hta (dot)com), JEOL (www(dot)jeol(dot)com), Keyence (www (dot)keyence(dot)com), Kramer (www(dot)kramerscientific (dot)com), Leica Microsystems (www(dot)leica(dot)com), Meiji Techno America (www(dot)meijitechno(dot)com), Motic Instruments (www(dot)motic(dot)com), Nikon Instruments (www(dot)nikoninstruments(dot)com), Ocean Optics (www(dot)oceanoptics(dot)com), Olympus (www (dot)olympusamerica(dot)com), OPTIKA Microscopes (www(dot)optikamicroscopes(dot)com), Phenom-World (www(dot)phenom-world(dot)com), Prior Scientific (www (dot)prior(dot)com), Warner (www(dot)warneronline(dot) com), and the like.

Microscope systems of the present disclosure may include a stationary or movable imaging stage. Moveable imaging stages may computer controlled having one or more actuators or motors in electrical communication with a processor for moving the stage in accordance with signals or instructions received from the processor. Automated moveable imaging stages find use in scanning one or more regions of a slide or specimen. Suitable microscope systems may also include those having a stationary imaging stage and a moveable objective or objective turret. Similar to an automated moveable imaging stage, a moveable objective or turret may be computer controlled having one or more actuators or motors in electrical communication with a processor for moving the objective or turret, e.g., relative to the stationary imaging stage, in accordance with signals or instructions received from the processor.

Devices and systems of the present disclosure may include one or more microscope slides. Slides that may be utilized in the subject devices and systems include specimen slides having a specimen applied thereto. Slides with an applied specimen may include slides with an applied hematological specimen, where the hematological specimen (e.g., blood, bone marrow, etc.) is smeared on the slide. Specimen slides may include those stained in accordance with one or more histological staining techniques.

As used herein, histology stains refer to those stains used in microscopic analysis of the cellular anatomy and/or morphology of cells obtained from a multicellular organism. Histology stains generally include at least one dye that stains one or more cell types and/or components of one or more cell types a contrasting color. Histology stains may also include at least one counter-stain that stains the rest of the cells or the rest of the cell a different color. Histological techniques, stains and staining methods are well-known and include but are not limited to those described in Kierman. *Histological and histochemical methods: Theory and practice*. Oxford: Butterworth/Heinemann, 1999 and Bancroft & Stevens. *Theory and practice of histological techniques*. New York, N.Y.: Churchill Livingstone, 1996; the disclosures of which are incorporated herein by reference in their entirety.

Histological staining techniques can be specific, staining one or more particular cells in a specific way, or non-specific, staining essentially all cells or most cells in the same or similar way. Histology stains include but are not limited to e.g., Alcian blue stains, Aniline blue stains, Azan stains, Biebrich scarlet-acid fuchsin stains, Carbol-fuchsin stains, Chrome alum/haemotoxylin stains, Congo Red stains, Crystal violet stains, Fast Red stains, Hematoxylin and Eosin (H&E) stains, Iron Hematoxylin stains, Isamin blue/eosin stains, Jenner's stains, Mallory's Phosphotungstic Acid Hematoxylin (PTAH) stains, Mallory's Trichrome stains, Masson stains, Malachite Green stains, Methyl Green-Pyronin (MGP) stains, Nissl and methylene blue stains, Nissl stains, Oil Red O stains, Orcein stains, Osmic Acid stains, Osmium Tetroxide stains, Papanicolaou stains, Periodic Acid-Schiff (PAS) stains, Reticulin stains, Romanowsky stains, Safranin O stains, Silver stains, Sudan Black and osmium stains, Toluidine-blue stains, Trichrome AB, Trichrome LG, Trypan Blue stains, van Gieson stains, Verhoff's stains, Weigert's resorcin-fuchsin stains, and the like.

Histological stains include Romanowsky stains. Romanowsky stains are generally neutral stains composed of various components including but not limited to methylene blue (e.g., Azure B) and eosin (e.g., Eosin Y) dyes. Azures are basic dyes that bind acid nuclei and result in a blue to purple color. Eosin is an acid dye that is attracted to the alkaline cytoplasm producing red coloration. Romanowsky stains vary and include various formulations including those containing various azure and eosin analogs. Romanowsky stains and their mechanisms of staining are well-known and described in e.g., Horobin & Walter. *Histochemistry* (1987) 86:331-336; Marshall et al. *J Clin Pathol* (1978) 31(3):280-2; Marshall et al. *J Clin Pathol.* (1975) 28(11):920-3; *J Clin Pathol* (1975) 28(8):680-5; the disclosures of which are incorporated herein by reference.

Romanowsky stains include but are not limited to Giemsa Stain, Wright Stain, Wright Giemsa Stain, Jenner Stain, Jenner-Giemsa Stain, Leishman Stain, May Grunwald Stain, May Grunwals Giemsa Stain, and the like. Each Romanowsky stain may exist in various formulations either as derived from various different recipes or as supplied from various providers. Romanowsky stain formulations may include various stain components including but not limited to e.g., methylene blue, azure A, azure B, azure C, toluidine blue, thionine, methylene violet Bernthsen, methyl thionoline, thionoline, eosin, eosin Y, tribromofluorescein, fluorescein, thiazine dyes, and the like. Romanowsky stain formulations may include various solvents to dissolve stain components including aqueous and organic solvents including but not limited to e.g., water and alcohols including but not limited to e.g., methanol, ethanol, isopropyl alcohol, etc.

The histological stains and components thereof include those commercially available from such suppliers including not limited to e.g., Sigma Aldrich, Thermo Fisher Scientific, Avantor Proformance Materials, VWR International, Polysciences Inc., and the like.

Useful slides (i.e., microscope slides), although readily available, may vary in shape and dimension. The primary surface if a slide (i.e., the surface to which the specimen is applied) may be essentially square, essentially rectangular, etc. Slides are commonly available with primary surface dimensions including but not limited to e.g., 25 mm×25 mm, 25 mm×75 mm, 25 mm×76 mm, 26 mm×75 mm, 26 mm×76 mm, 27 mm×46 mm, 28 mm×48 mm, 38 mm×75 mm, 50 mm×75 mm, 51 mm×75 mm, 51 mm×76 mm, 52 mm×76 mm, 76 mm×102 mm, 83 mm×102 mm, 102 mm×127 mm, 114 mm×152 mm, 127 mm×178 mm, and the like.

Rectangular slides may be referred to as having a long axis (e.g., the x-axis as depicted in FIG. 2) and a short axis (e.g., the y-axis as depicted in FIG. 2), where such axes are defined relative to the primary surface of the slide. Slide thickness (i.e., slide dimensions in the z-axis) will vary and may range from 0.5 mm or less to 2 mm or more including but not limited to e.g., 0.5 mm thick, 1 mm thick, 1.2 mm thick, 1.4 mm thick, 1.6 mm thick, etc. Slides may or may not have a "frosted area", where a frosted area generally refers to any area of the slide configured for adding (writing, printing, etching, adhering, etc.) information (e.g., specimen information, patient information, assay information, date, time, etc.) to the slide, whether or not the area is actually "frosted". As described above, the frosted area of the slide may also be referred to as the specimen information area or the patient information area, as such terms are used interchangeably herein. Slides will generally be constructed of glass but may also, in some instances, be constructed of various polymers including but not limited to plastics (e.g., polystyrene, acrylic, and the like).

As noted above, one or more slides may be moved through or about a slide analysis system through the use of a slide conveyor. Slide conveyors will vary greatly and may include apparatus that move a single slide at a time or multiple slides simultaneously (e.g., where slides are transported with or without the use of a slide carrier, described in more detail below). For example, in some instances, a slide conveyor may be a robotic arm or other device that includes a robotic gripper configured to grab a slide and convey it to a desired location. In some instances, a slide conveyor may be a conveyor belt or other device upon which a slide may be placed to convey it to a desired location. In some instances, a slide conveyor may be an elevator or other device which may raise or lower a slide or raise or lower a plurality of slides (e.g., as housed in a slide carrier) to convey the one or more slides a desired location. Slide conveyors may be rotatable or may be capable of rotating a slide carrier, e.g., the affect a change in slide orientation as described above.

As noted above, devices and systems of the present disclosure may include a slide carrier and a slide conveyor of the subject systems may, in some instances, utilize a slide carrier for transporting slides. Suitable slide carriers will vary and may, e.g., include those slide carriers having one or more slots dimensioned to hold a slide. Such devices will generally include one or more slots or contact points capable of holding a slide during transport through one or more areas of an automated slide analysis system.

The slide holding capacity of slide carriers will vary depending on the particular configuration, e.g., a slide carrier have a capacity of one slide to 20 or more, including but not limited to e.g., from one to 20 slides, from one to 19 slides, from one to 18 slides, from one to 17 slides, from one to 16 slides, from one to 15 slides, from one to 14 slides, from one to 13 slides, from one to 12 slides, from one to 11 slides, from one to 10 slides, from one to 9 slides, from one to 8 slides, from one to 7 slides, from one to 6 slides, from one to 5 slides, from one to 4 slides, from one to 3 slides, one or 2 slides, from 2 to 20 slides, from 2 to 19 slides, from 2 to 18 slides, from 2 to 17 slides, from 2 to 16 slides, from 2 to 15 slides, from 2 to 14 slides, from 2 to 13 slides, from 2 to 12 slides, from 2 to 11 slides, from 2 to 10 slides, from 2 to 9 slides, from 2 to 8 slides, from 2 to 7 slides, from 2 to 6 slides, from 2 to 5 slides, from 2 to 4 slides, 2 or 3 slides, from 5 to 20 slides, from 5 to 19 slides, from 5 to 18 slides, from 5 to 17 slides, from 5 to 16 slides, from 5 to 15 slides, from 5 to 14 slides, from 5 to 13 slides, from 5 to 12 slides, from 5 to 11 slides, from 5 to 10 slides, from 5 to 9 slides, from 5 to 8 slides, from 5 to 7 slides, 5 or 6 slides, from 10 to 20 slides, from 10 to 19 slides, from 10 to 18 slides, from 10 to 17 slides, from 10 to 16 slides, from 10 to 15 slides, from 10 to 14 slides, from 10 to 13 slides, from 10 to 12 slides, 10 or 11 slides, etc.

The path a slide takes en route from one location to another, e.g., as transported by a robotic arm or other device having a robotic gripper, as transported within a slide carrier, as transported using a slide elevator, etc., may be referred to as a slide transport path. Systems of the present disclosure may include a digital imager positioned along a slide transport path, e.g., for imaging the specimen information area of a slide. For example, a subject system may include a digital imager positioned along a slide transport path to or from the microscope component of the system utilized in imaging the specimen. In some instances, a system of the subject disclosure may include a digital imager positioned along the slide transport path from a slide loading or preparation component to the microscope component of the system. In some instances, a system of the subject disclosure may include a digital imager positioned along the slide transport path from the microscope component of the system to a slide storage or slide disposal component of the system.

As a non-limiting example of an automated slide analyzer, such as an automated hematology analyzer including a digital morphology system (also referred to in some instances as an automated digital image-based hematology system), such as described in U.S. Provisional Patent Application No. 62/269,535, the disclosure of which is incorporated herein by reference in its entirety, may be configured to obtain patient-tagged specimen data. Such a system may include a slide maker stainer system and a digital morphology subsystem and may be further configured to include a digital imager for imaging a specimen information area of a slide, e.g., while a slide is en route from the slide maker stainer system to the digital morphology subsystem or after imaging in the digital morphology subsystem, e.g., while the slide is en route to a storage area or a waste collection area.

A "slide maker stainer system" generally refers to a system for automatically preparing and staining hematological slides. Such systems may include components for the automated analysis of prepared and stained slides such as a digital morphology subsystem. The subsystem may include a digital microscope. The subsystem may further include components for loading a slide, preparing a slide for imaging and/or imaging the slide including e.g., slide loader components, components of an oil application system (e.g., for applying oil to the smear for high magnification morphology analysis), vibration isolation components, slide storage and/or disposal components (e.g., an oily slide carrier), and the like.

Figure 11:
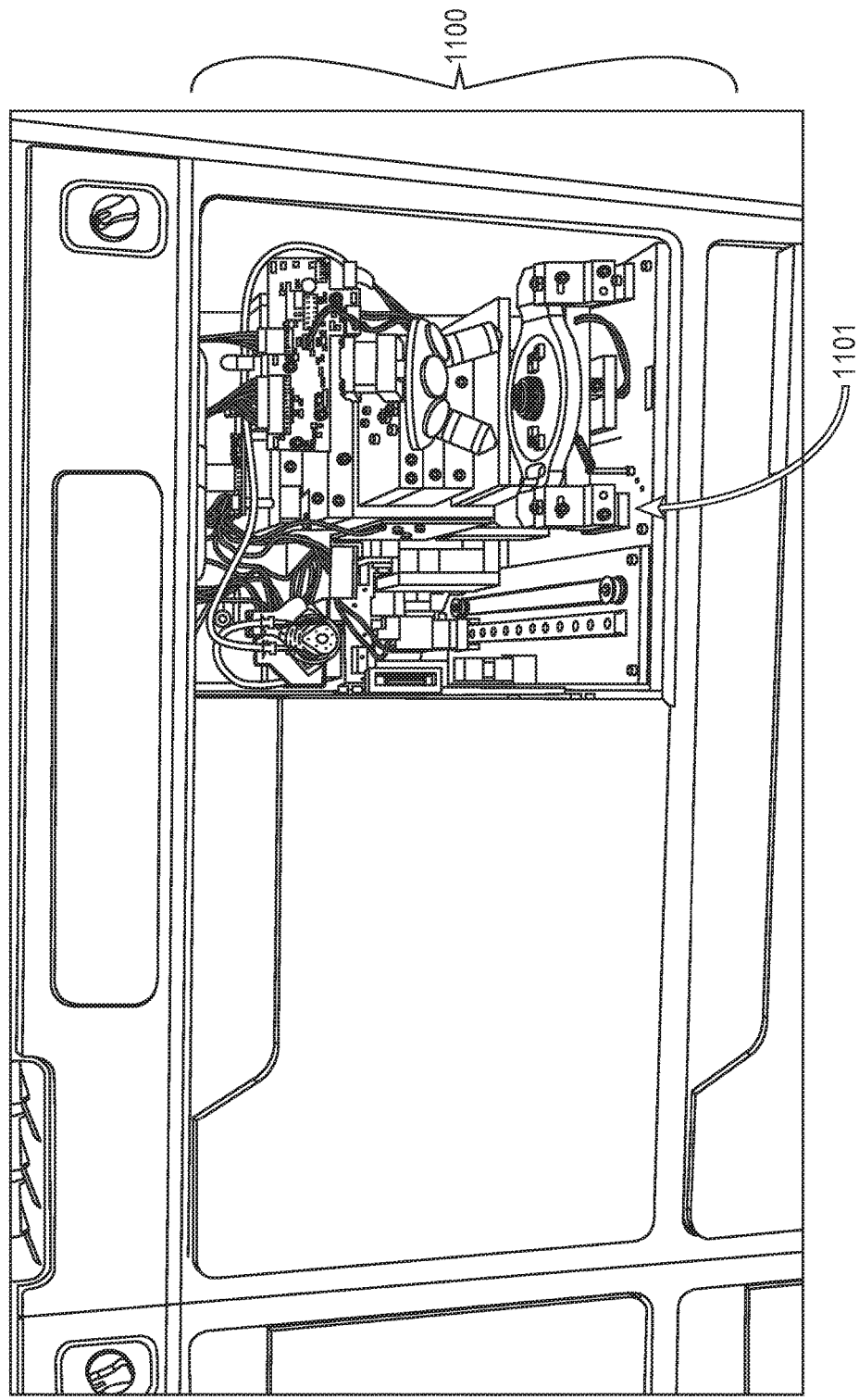
FIG. 11 shows a slide maker stainer system that includes a digital morphology subsystem.

In some instances, when the slide maker stainer system includes a digital morphology subsystem, the digital morphology subsystem may be located in a lower compartment of the system beneath the slide maker stainer slide processing deck. An example of this configuration is shown in FIG. 11, which shows a lower compartment (1100) of a slide maker stainer system that includes digital morphology subsystem (1101). When configured in this way, the digital morphology subsystem may include a slide carrier elevator that lowers slide carriers containing slides from an upper processing deck to the digital microscope of the subsystem in the lower compartment.

Figure 12:
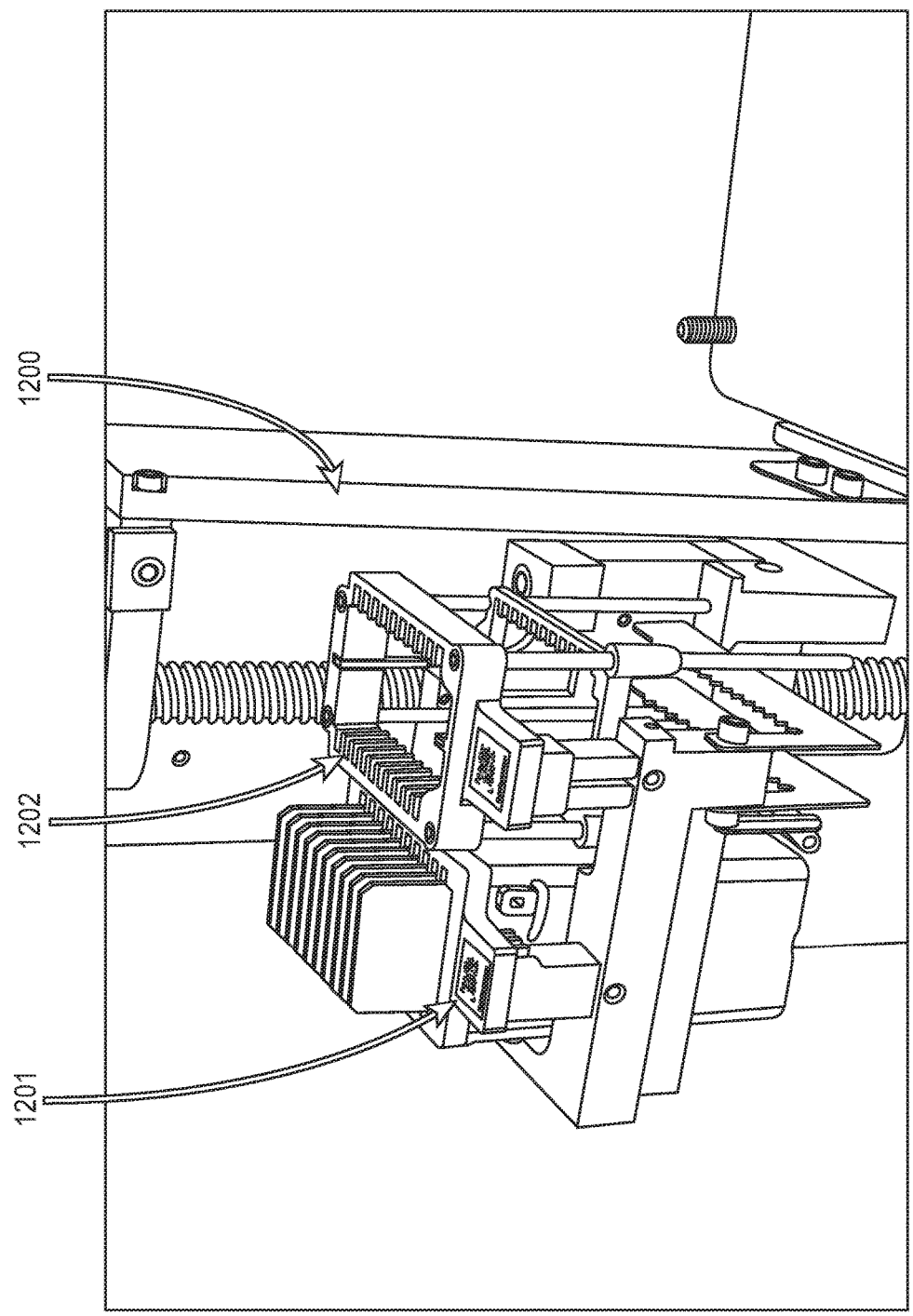
FIG. 12 shows a slide carrier elevator and slide carriers of a slide maker stainer.
Figure 13:
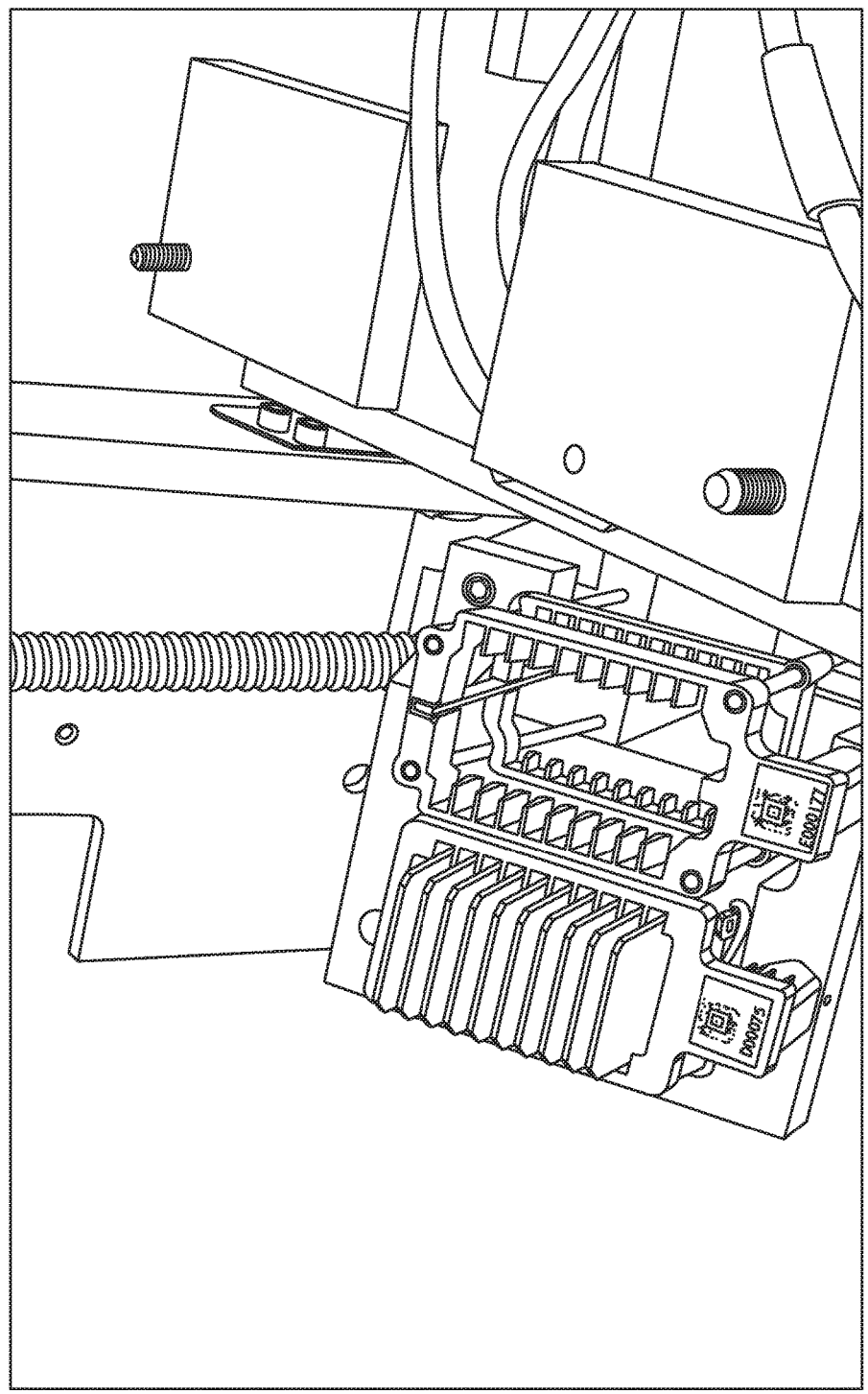
FIG. 13 shows rotation of slide carriers by a slide carrier elevator as the elevator lowers the slide carriers to a lower compartment of a slide maker stainer.
Figure 14:
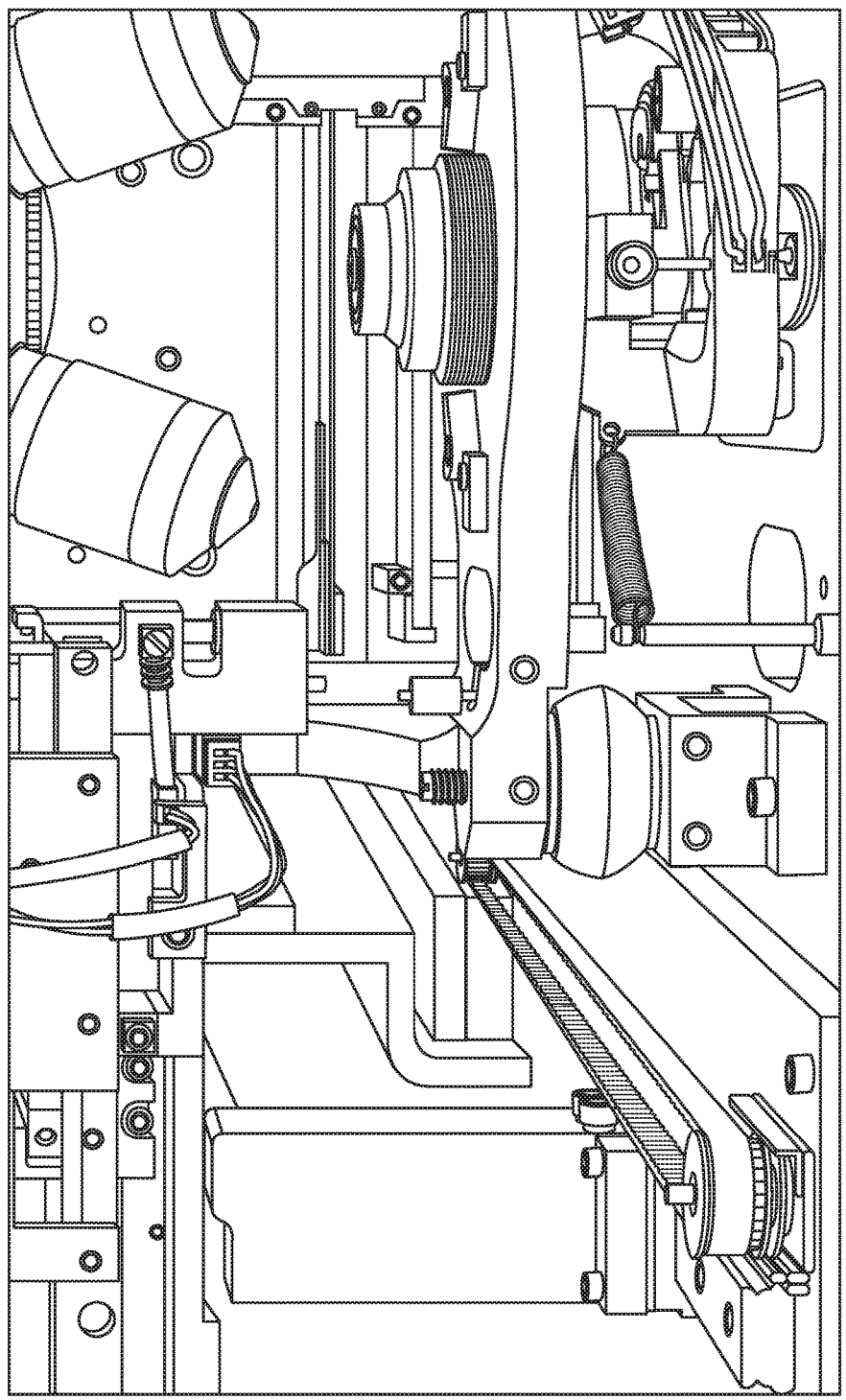
FIG. 14 shows a slide being placed on the stage of a digital microscope of a digital morphology subsystem of a slide maker stainer system, which slide was retrieved from a slide carrier present in a slide carrier elevator of the subsystem.

An example of such an slide conveyor elevator is shown in FIG. 12. Shown is an upper portion (1200) of slide carrier elevator which is holding an oily slide carrier (1201) and a slide carrier (1202), such that slides present in the slide carriers are initially held in a vertical orientation. In this example, as the slide carriers are lowered by the elevator to the lower compartment of the slide maker stainer system for digital morphology analysis, the elevator rotates the slide carriers such that the slides present in the slide carriers are in a horizontal orientation when they reach the lower compartment. This horizontal orientation facilitates the removal of slides from the slide carriers and placement of the slides in the horizontal orientation on a stage of the digital microscope. Rotation of the slide carriers by the elevator as the elevator lowers the slide carriers to the lower compartment is shown in FIG. 13. FIG. 14 shows a slide being placed on the stage of a digital microscope of a digital morphology subsystem, which slide was retrieved from a horizontally-oriented slide carrier present in a slide carrier elevator of the subsystem.

Using the above described slide maker stainer system with digital morphology subsystem as a reference. Systems of the present disclosure may include e.g., a digital imager positioned along the slide carrier path to capture an image of the specimen information area of the slides, e.g., before, during or after the slides are lowered using the slide carrier elevator. Systems of the present disclosure may include e.g., a digital imager positioned along the slide path to capture an image of the specimen information area of the slide, e.g., before, during or after removal of the slide from the slide carrier, before, during or after the slide is placed on the stage of a digital microscope of a digital morphology subsystem, etc. As such, in such a system the specimen information area of the slide may be imaged in a vertical or horizontal orientation. As such, in such a system the specimen information area of the slide may be imaged before, during or after the slide is rotated from one orientation to another, e.g., from a vertical orientation to a horizontal orientation.

In some instances, the systems of the instant disclosure include image processing circuitry. Such image processing circuitry may be programmed and/or contain instructions to perform one or more tasks related to processing a digital image received from an image capture device. For example, in some instances, the image processing circuitry is programmed to extract one or more feature values (e.g., a density distribution feature value as described above) from a digital image obtained from digital storage or generated by an image capture device. In some instances, the image processing circuitry is programmed to make a comparison between extracted values a reference value, e.g., as stored in a library, according to the methods described herein.

In some instances, image processing circuitry may be programmed to perform one or more steps in isolation or in combination of the methods described herein including but not limited to e.g., generating a mask of the subject digital image, determining an ROI of the subject digital image, extracting one or more feature values, etc. In some instances, image processing circuitry may be further programmed to make a comparison between extracted feature values or an extracted feature value and a reference value or threshold.

In addition to the direct image processing steps, image processing circuitry may be, or may have an operable connection with additional circuitry, configured to perform one or more additional functions including but not limited to e.g., receive a digital image from an image capture device, retrieve a digital image from memory, retrieve a reference value from memory, store a processed image to memory, store a value obtained from a processed image to memory, store the result of a comparison to memory, etc.

In some instances, the systems as described herein further include a signal system where the signal system may be configured to report the result of a comparison or assessment. Such signal systems will vary depending on the particular configuration of the device and or system and may include but are not limited to e.g., an alarm, an indicator light, a display (e.g., a computer monitor, a graphical user interface (GUI), etc.), a printer configured to print, e.g., onto tangible media (including e.g., paper or tape), and the like. In some instances, the signal system indicates, e.g., sounds, lights up, or otherwise displays, to a user when a morphology assessment area is identified, when a morphology assessment area cannot be identified, when a slide is identified as having or not having machine readable information in the specimen information area of the slide, etc.

In some instances, the signal system indicates, e.g., sounds, lights up, or otherwise displays, to a user the result of an assessment according to one or more of the methods described herein. For example, in some instances, the system may include a display configured to report a result of one or more assessments generated according to the methods described herein. In some instances, the system may transmit the result to a remote display or transmit the result as data (e.g., transmit to a data store, transmit to a user via electronic means (e.g., email), etc.). In some instances, a system may report the result of an assessment, e.g., the location of the morphology assessment area, as part of a larger report, e.g., as part of a cell count or complete hematological report.

The image processing circuitry is specifically configured or programed to perform the functions according to the methods as described herein, including image processing functions, feature value extraction functions and comparison tasks, and may include at least one data processing unit for performing data related functions.

By "data processing unit", as used herein, is meant any hardware and/or software combination that will perform the functions required of it. For example, any data processing unit herein may be a programmable digital microprocessor such as available in the form of an electronic controller, mainframe, server or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based).

In some instances, the components of the systems as described herein may be connected by a wired data connection. Any suitable and appropriate wired data connection may find use in connecting the components of the described systems, e.g., as described herein, including but not limited to e.g., commercially available cables such as a USB cable, a coaxial cable, a serial cable, a C2G or Cat2 cable, a Cat5/Cat5e/Cat6/Cat6a cable, a Token Ring Cable (Cat4), a VGA cable, a HDMI cable, a RCA cable, an optical fiber cable, and the like. In some instances, e.g., where data security is less of a concern, wireless data connections may be employed including but not limited to e.g., radio frequency connections (e.g., PAN/LAN/MAN/WAN wireless networking, UHF radio connections, etc.), an infrared data transmission connection, wireless optical data connections, and the like.

The devices and systems of the instant disclosure may further include a "memory" that is capable of storing information such that it is accessible and retrievable at a later date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer harddrive, CD-ROM, floppy disk, portable flash drive and DVD are all examples of permanent memory. Random Access Memory (RAM) is an example of non-permanent memory. A file in permanent memory may be editable and re-writable.

Substantially any circuitry can be configured to a functional arrangement within the devices and systems for performing the methods disclosed herein. The hardware architecture of such circuitry, including e.g., a specifically configured computer, is well known by a person skilled in the art, and can comprise hardware components including one or more processors (CPU), a random-access memory (RAM), a read-only memory (ROM), an internal or external data storage medium (e.g., hard disk drive). Such circuitry can also comprise one or more graphic boards for processing and outputting graphical information to display means. The above components can be suitably interconnected via a bus within the circuitry, e.g., inside a specific-use computer. The circuitry can further comprise suitable interfaces for communicating with general-purpose external components such as a monitor, keyboard, mouse, network, etc. In some embodiments, the circuitry can be capable of parallel processing or can be part of a network configured for parallel or distributive computing to increase the processing power for the present methods and programs. In some embodiments, the program code read out from the storage medium can be written into a memory provided in an expanded board inserted in the circuitry, or an expanded unit connected to the circuitry, and a CPU or the like provided in the expanded board or expanded unit can actually perform a part or all of the operations according to the instructions of the programming, so as to accomplish the functions described.

In addition to the components of the devices and systems of the instant disclosure, e.g., as described above, systems of the disclosure may include a number of additional components, such as data output devices, e.g., monitors and/or speakers, data input devices, e.g., interface ports, keyboards, etc., actuatable components, power sources, etc.

Computer Readable Media

The instant disclosure includes computer readable medium, including non-transitory computer readable medium, which stores instructions for methods described herein. Aspects of the instant disclosure include computer readable medium storing instructions that, when executed by a computing device, cause the computing device to perform one or more steps of a method as described herein.

Aspects of computer readable media of the present disclosure include media having instructions that trigger components of a system, including e.g., one or more components of the systems as described herein. In some instances, such instructions may trigger components of a system to make an assessment of the morphology assessment area. Such components that may be triggered include components of an automated hematological morphology analyzer. In some instances, instructions may trigger components of a system to perform a step of comparing or ranking. Any convenient comparison or ranking consistent with the above described methods may be triggered. In some instances, the instructions may trigger a ranking of density distribution feature values, including e.g., density distribution feature values associated with multiple ROIs, including multiple ROIs of an image, multiple ROIs each associated with a separate image, etc.

In some instances, the instructions may trigger further analysis. For example, in some instances, the instructions may trigger further extraction of feature values, including e.g., extracting a second or subsequent density distribution feature value. Subsequent density distribution feature value triggered to be extracted may be associated with various aspects of one or more images including e.g., with each ROI of a plurality of ROIs, with each ROI of each image of a plurality of images, etc. In some instances, the instructions may trigger the application of a threshold or a comparison to a reference value, where such thresholds and/or reference values may be stored on the same or different computer readable medium as the instructions. For example, in some instances, the instructions may include applying a threshold based on a density distribution value, or subsequent distribution values, e.g., to exclude one or more images of a plurality of images from an analysis.

In certain embodiments, instructions in accordance with the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

The following examples are offered by way of illustration and not by way of limitation.

EXAMPLES

Example 1: Automated Identification of Monolayer Analysis Area of a Blood Smear A set of 21 monolayer images of blood smears prepared from normal subjects were utilized for algorithm testing. The images were acquired in continuous mode along the central line of the blood smear with no spatial gaps in between consecutive images. Single field monolayer images were captured at 1456×1936 resolution, corresponding to physical dimensions of 660 μm×880 μm in the object space (i.e., area on the slide). The captured raw images were color in 24 bit depth BGR (blue, green, red) format. Each separate color channel image was 8 bit. Each image was acquired at optical z-axis focal position. During focusing, fast Fourier transform (FFT) focus metric was used to calculate the position of the best focused image from each acquired z-axis stack.

Each image was cropped to remove darkened corners (i.e., "vignetting") by cropping each x-axis edge by 182 pixels and each y-axis edge by 242 pixels. The resulting cropped images, 1092×1452 pixels, were next processed for monolayer segmentation (i.e., separation of objects in the image from each other and image background). In the instant example, segmentation segmented RBCs from each other and image background.

Input 24 bit full-color BGR images (1092×1452) were split into grayscale individual color channels to generate "blue", "green" and "red" channel images each represented by an 8 bit grayscale image of 1092×1452 resolution.

The blue channel image was input into a Soille threshold procedure for separation of foreground and background using the blue channel image histogram pixel values. The procedure output a "foreground" mask of the blue channel as a binary image of 1092×1452 resolution (pixels with intensity values below the Soille threshold=1, pixels with intensity values above the Soille threshold=0). In the instant example, foreground masks were generated only for the blue channel.

The raw masks were found, in some cases, to contain "holes" in the middle of white spots corresponding to the RBCs. Black holes of variable size depending on hematocrit (HCT) were also found, thus the "black" area to be "closed" varied respectively. The holes in the foreground masks were closed to generate continuous RBC shapes. Hole closure was performed using the generated binary 1092×1452 resolution blue foreground masks as input into a hole closing procedure. To choose the size of the hole closing area ("Hole Closing Size"), the ratio ("Foreground Ratio") was computed from the number of pixels in the foreground (pixels with value=1) versus the total number of pixels in the mask (1452×1092). The following table (Table 1) was utilized to determine the correct hole closing size for a given mask. The hole closing procedure was executed for each foreground mask.

TABLE 1

| Hole closing size for different foreground ratios. | |
|---|---|
| Foreground ratio (%) | Hole closing size (pixels) |
| 80%-100% | 30 |
| 60%-79% | 40 |
| 20%-59% | 60 |
| 0%-19% | 80 |

Noise reduction was performed following the hole closing procedure. In general, the masks were cleaned of holes that had been filled in, removing any that were too large to be the centers of cells (i.e., greater than 100 pixels, 1 pixel corresponds to 0.454 μm). The cleaned holes were then added to the original foreground mask and any small objects ("specks", less than 20 pixels) in the final foreground were removed. The resulting output was a final foreground mask for the blue channel (binary image, 1092×1452). Watershed segmentation was performed using the final foreground mask for the blue channel as input to output a binary mask of separated cells with large objects (greater than 500 pixels) removed.

Various quantitative parameters ("features") were extracted for each original image. Various binary masks (revealing separated cells) were applied to the original full-color image (24 bit, BGR) and individual channel images (8 bit, Blue, Green, Red). Color features were calculated using individual color channel images, white non-color images were calculated by using binary masks generated for the blue channel image.

As noted above, non-color features were calculated from the binary mask cleaned of large objects as described, and thus watershed output was used as input for non-color feature calculation. Non-color feature calculation output included the following: CellsCount, MeanObjectSize, MedianObjectSize, StdDevObjectSize and CvObjectSize (StdDevObjectSize/MeanObjectSize).

Following feature calculation, the monolayer analysis area was determined based on grading all images and choosing the image with the best score. The coordinates corresponding to the center of the image with the best score was used as the starting position for 20× serpentine path slide scanning.

In the instant example, coefficient of variation (CV) index was utilized for monolayer analysis area identification. The CV index classification algorithm used was based on the coefficient of variation of object size within each individual 20× monolayer image. The CV index classification algorithm used was based on two features (CVObjectSize and CellCount) and ranks the images in order based on the calculated features. The highest ranked image (i.e., the image with the best score) was chosen by the software as the monolayer analysis area (i.e., the "optimal spot" for blood smear monolayer analysis and specimen assessment). The CV index algorithm proceeded as follows:

a) From all 21 images in the monolayer data set, images having calculated cell counts ("CellsCount") less than or equal to 100 (i.e., images with less than 100 cells) were excluded from further analysis.

b) The remaining images were sorted according to their values of CvObjectSize in ascending order (i.e., image with the smallest score was ranked at the top of the sort).

c) The sorted list was truncated at its seventh member. From this list of six remaining images with the smallest CvObjectSize values, the image with the highest number of cells (i.e., the maximum value of CellsCount) was chosen.

d) The chosen image with the highest number of cells was compared to a threshold value for CellsCount of 4500 (threshold empirically derived). If the chosen image had a total cell count number smaller than 4500 (CellsCount<4500) then the chosen image was used for determining the monolayer "optimal spot".

e) If the chosen image had a total cell count number greater than 5000 cells (4500<CellsCount<5000), then the sample from which the image was derived was most likely a high HCT sample. In these cases, the chosen image typically locates at the boundary to the feather edge. Therefore, the chosen image was assigned a designation of "r" and the rest of the images in the monolayer data set were numbered according to their x-axis position relative image "r", assuming the that the monolayer scan started from the thick area of the smear (image number "0") and proceeded to the feather edge (image number "20"). According to this numbering convention, when the total cell count number was in the above range, the image having a designation of "r-2" was selected for determining the monolayer "sweet spot".

f) If all six images of the truncated set were found to have total cell counts larger than 5000 (CellsCount>5000), the scoring algorithm was no longer applicable. When a truncated image set where all images have total cell counts above 5000 was detected, the system rejected the slide and reported that a monolayer analysis area could not be identified.

Figure 7:
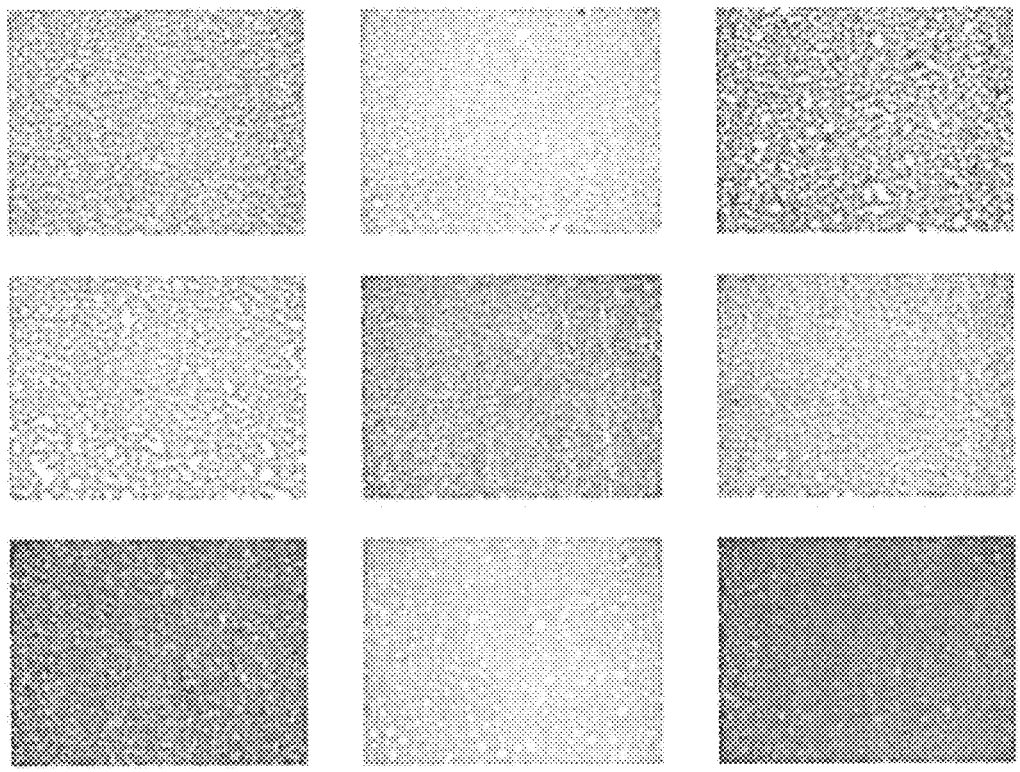
FIG. 7 provides examples of images annotated as acceptable for monolayer localization by an embodiment of an algorithm described herein.
Figure 8:
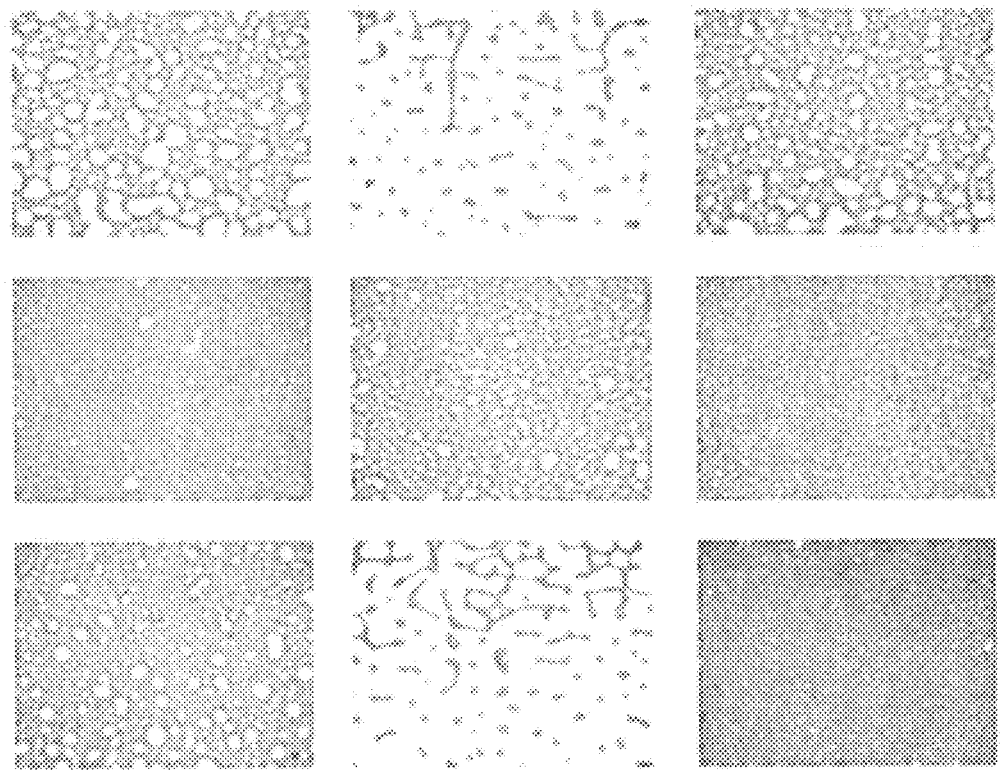
FIG. 8 provides examples of images annotated as unacceptable for monolayer localization by an embodiment of an algorithm described herein.

Examples of images annotated by the algorithm as acceptable and unacceptable for monolayer localization are provided in FIG. 7 and FIG. 8, respectively.

Example 2: Automatically Obtaining and Associating Non-machine-readable Slide Information with Digital Microscopic Specimen Images When analyzing cell morphology in an automated morphology analyzer or combination slide-maker/analyzer, tracking of slides that do not contain a machine-readable code is conventionally performed manually by a system operator. Similarly, when a slide contains both machine-readable information and non-machine-readable information and automated tracking is utilized, the non-machine-readable information is lost in conventional systems.

The instant example describes a process that allows for automated tracking of slides that do not contain a machine-readable code and/or the automated retention of non-machine-readable slide information during automated slide tracking of slides containing both machine-readable information and non-machine-readable information.

Figure 9:
FIG. 9 provides images of slides demonstrating the wide variety of machine-readable information, non-machine-readable information and combinations thereof that may be present on slides analyzed by an automated morphology analyzer.

In the instant example, an automated imaging system was used that includes a digital microscope and a slide imager position upstream (i.e., before) the digital microscope such that and machine-readable information and/or non-machine-readable information present on the slide is imaged before the slide reaches the microscope. The slide imager system used is capable capturing and processing both machine-readable information (e.g., 1D barcode or 2D barcode) and non-machine-readable information (e.g., hand written annotations on the slide frosted area). FIG. 9 provides images of slides demonstrating the wide variety of machine-readable information, non-machine-readable information and combinations thereof that may be present on slides analyzed by an automated morphology analyzer.

Figure 10:
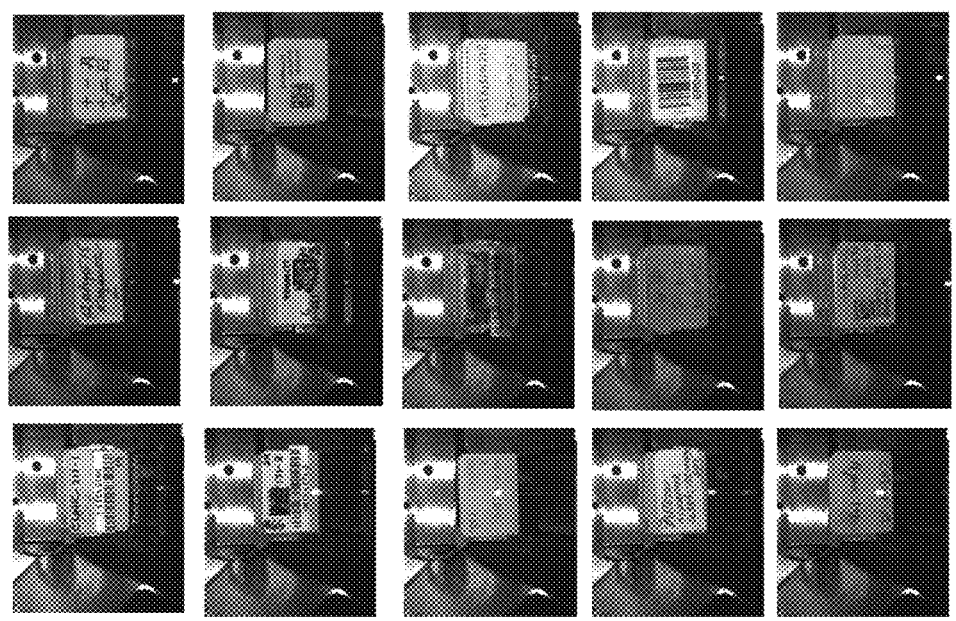
FIG. 10 provides exemplary images of machine-readable information and non-machine-readable information present on slides taken by an imager according to an embodiment of the methods described herein.

In the instant example, an automated method was used to capture and machine-readable information and non-machine-readable information present on a slide and cross-reference this information with images taken by the digital microscope and any corresponding analysis of the microscope image(s) performed by the system. FIG. 10 provides exemplary images of the machine-readable information and non-machine-readable information present on a slide taken by the imager. Such images are stored and linked to images of the specimen taken by the digital microscope (e.g., RBC images, WBC images, etc.) and any corresponding analysis of the microscope image(s) performed by the system. Accordingly, any corresponding results are easily identified as being associated with the slide image as such images are stored together and linked in the system.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of assessing a blood smear on a slide using an automated digital cell morphology analyzer, the method comprising:
   a) collecting a plurality of z-axis images along an optical z-axis at an initial xy-position of the blood smear by varying the distance between the slide and an objective lens;
   b) comparing the z-axis images of the plurality to identify a starting focal z-plane;
   c) moving the slide or the objective lens relative to an x-axis of the blood smear through a plurality of xy-locations;
   d) acquiring a plurality of z-axis images based on the starting focal z-plane at each of the plurality of xy-locations and selecting an optimal z-axis image for each xy-location;
   e) analyzing a region of interest (ROI) within each optimal z-axis image to extract a density distribution feature value for each ROI of each image;
   f) identifying a morphology assessment area of the blood smear based on a comparison of the density distribution feature values; and g) assessing the morphology assessment area using an automated digital cell morphology analyzer.

2. The method according to claim 1, wherein the x-axis of step c) is the central line of the slide.

3. The method according to claim 1, wherein varying the distance between the slide and the objective lens is performed in distinct z-axis steps.

4. The method according to claim 1, wherein moving the slide or the objective lens relative to the x-axis of the blood smear is performed at distinct x-axis steps.

5. The method according to claim 1, wherein the comparison of the density distribution feature values comprises ranking the density distribution feature values.

6. The method according to claim 1, wherein the analyzing comprises extracting a second density distribution feature value for each ROI of each image.

7. The method according to claim 6, wherein the identifying further comprises applying a threshold based on the second density distribution value to exclude one or more images of the plurality.

8. The method according to claim 6, wherein the identifying is based on ranking each image of the plurality according to their associated extracted first cellular feature value and the second cellular feature value.

9. The method according to claim 1, wherein the processing comprises varying a size of the ROI used for analysis.

10. The method according to claim 9, wherein the x-axis and the y-axis of the ROI are varied equally.

11. The method according to claim 9, wherein the x-axis and the y-axis of the ROI are varied unequally.

12. The method according to claim 1, wherein the analyzing comprises splitting each optimal z-axis image into individual color channels.

13. The method according to claim 1, wherein the analyzing comprises separating foreground objects from background objects by generating a foreground mask for each optimal z-axis image.

14. The method according to claim 13, wherein the foreground mask is generated for the blue channel.

15. The method according to claim 13, wherein generating the foreground mask further comprises closing holes in the foreground mask.

16. The method according to claim 13, wherein generating the foreground mask further comprises noise filtering.

17. The method according to claim 1, wherein the analyzing comprises segmenting each optimal z-axis image to generate a mask of separated cells.

18. The method according to claim 1, wherein the density distribution feature value is a non-color feature.

19. The method according to claim 1, wherein the density distribution feature value is a color feature.

20. The method according to claim 1, wherein the density distribution feature value is selected from the group consisting of: a cell count, a coefficient of variation (CV) index for a cell count, a cell size, a coefficient of variation (CV) index for a cell size, an index defining a cell shape, a coefficient of variation (CV) for an index for a cell shape, an index defining central pallor of the cell, an index defining cell color, a count of overlapping cells, or a combination thereof.

21. The method according to claim 1, wherein the comparing of step b) comprises applying a fast Fourier transform.

22. The method according to claim 1, wherein the acquired plurality of z-axis images at each of the plurality of xy-locations are continuous images with no xy-spatial gaps between them.

23. The method according to claim 1, wherein the length along the x-axis of the acquired plurality of z-axis images at each of the plurality of xy-locations comprises greater than 50% of the total length of the blood smear.

24. The method according to claim 1, wherein the assessing comprises scanning the morphology assessment area at a magnification greater than that used in the collecting and acquiring steps a) and c).

25. The method according to claim 1, wherein the method further comprises a quality check, wherein an extracted density distribution feature value is compared to a reference value to determine if the blood smear is sufficient quality for assessment.

26. The method according to claim 25, wherein the reference value is a range or a threshold.

27. The method according to claim 26, wherein the reference value is a cell count threshold.

28. A non-transitory computer readable medium storing instructions that, when executed by a computing device, cause the computing device to perform the steps of:
collecting a plurality of z-axis images along an optical z-axis at an initial xy-position of a blood smear;
comparing the z-axis images of the plurality to identify a starting focal z-plane;
obtaining a plurality of z-axis images based on the starting focal z-plane at distinct xy-positions along an x-axis of the blood smear;
selecting an optimal z-axis image for each distinct xy-position;
analyzing a region of interest (ROI) within each optimal z-axis image to extract a density distribution feature value for each ROI of each image;
identifying a morphology assessment area of the blood smear based on a comparison of the density distribution feature values; and
triggering assessment of the morphology assessment area by an automated hematological morphology analyzer.

29. The non-transitory computer readable medium according to claim 28, further storing instructions that, when executed by a computing device, cause the computing device to perform the step of ranking the density distribution feature values for each ROI of each image.

30. The non-transitory computer readable medium according to claim 28, wherein the analyzing further comprises extracting a second density distribution feature value for each ROI of each image.

31. The non-transitory computer readable medium according to claim 28, wherein the identifying further comprises applying a threshold based on the second density distribution value to exclude one or more images of the plurality.

* * * * *